United States Patent
Foerster

(10) Patent No.: US 7,285,124 B2
(45) Date of Patent: Oct. 23, 2007

(54) SINGLE-TAILED SUTURING METHOD

(75) Inventor: Seth A. Foerster, San Clemente, CA (US)

(73) Assignee: Arthrocare Corp, Austin, TX (US)

( * ) Notice: Subject to any disclaimer, the term of this patent is extended or adjusted under 35 U.S.C. 154(b) by 82 days.

(21) Appl. No.: 10/750,287

(22) Filed: Dec. 31, 2003

(65) Prior Publication Data

US 2004/0162579 A1   Aug. 19, 2004

Related U.S. Application Data

(63) Continuation of application No. 09/949,249, filed on Sep. 7, 2001, now abandoned, and a continuation of application No. 09/515,360, filed on Feb. 29, 2000, now Pat. No. 6,296,659.

(51) Int. Cl.
*A61B 17/04*   (2006.01)

(52) U.S. Cl. .................. 606/139; 606/148; 606/224; 606/228

(58) Field of Classification Search ................ 606/139, 606/148, 224, 228
See application file for complete search history.

(56) References Cited

U.S. PATENT DOCUMENTS

| | | |
|---|---|---|
| 2,600,395 A | 6/1952 | Domoj et al. |
| 4,186,921 A | 2/1980 | Fox |
| 4,319,428 A | 3/1982 | Fox |
| 4,792,336 A | 12/1988 | Hlavacek et al. |
| 4,946,377 A | 8/1990 | Kovach |
| 4,962,929 A | 10/1990 | Melton, Jr. |
| 4,987,665 A | 1/1991 | Dumican |
| 5,062,344 A | 11/1991 | Gerker |
| 5,217,495 A | 6/1993 | Kaplan et al. |
| 5,259,846 A | 11/1993 | Granger et al. |
| 5,263,984 A | 11/1993 | Li |
| 5,376,118 A | 12/1994 | Kaplan et al. |
| 5,405,352 A | 4/1995 | Weston |
| 5,450,860 A | 9/1995 | O'Connor |
| 5,540,703 A | 7/1996 | Barker, Jr. et al. |
| 5,667,528 A | 9/1997 | Colligan |
| 5,683,417 A | 11/1997 | Cooper |

FOREIGN PATENT DOCUMENTS

| | | |
|---|---|---|
| DE | 196 28 909 | 1/1998 |
| WO | WO96/17544 | 6/1996 |

*Primary Examiner*—Gary Jackson
(74) *Attorney, Agent, or Firm*—Richard R. Batt

(57) ABSTRACT

A suture loop is formed in a hollow braided suture by feeding one end of a length of suture through a part in the braid of the suture and into the inner lumen formed by the hollow braid. The braided configuration of the suture allows it to be expanded in diameter by pushing and reduced in diameter by pulling. Said end of suture is passed continuously through said inner lumen forming a loop of suture with a single tail. The loop may be tightened by pulling on said first end of the suture while pushing on said outer hollow braid. The loop may be locked by extending or pulling on said outer hollow braid to reduce its diameter and lock it down around said first end of the suture.

9 Claims, 40 Drawing Sheets

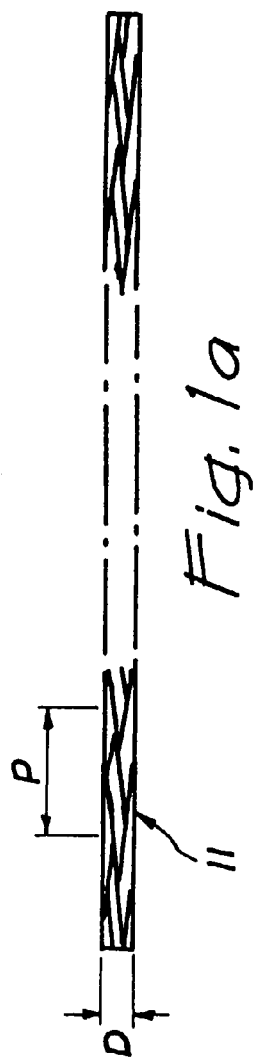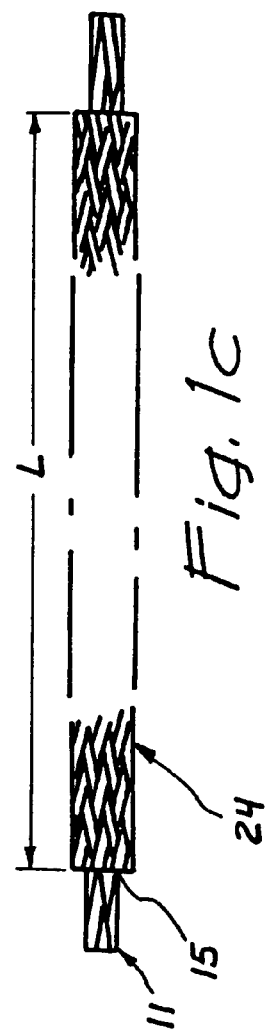

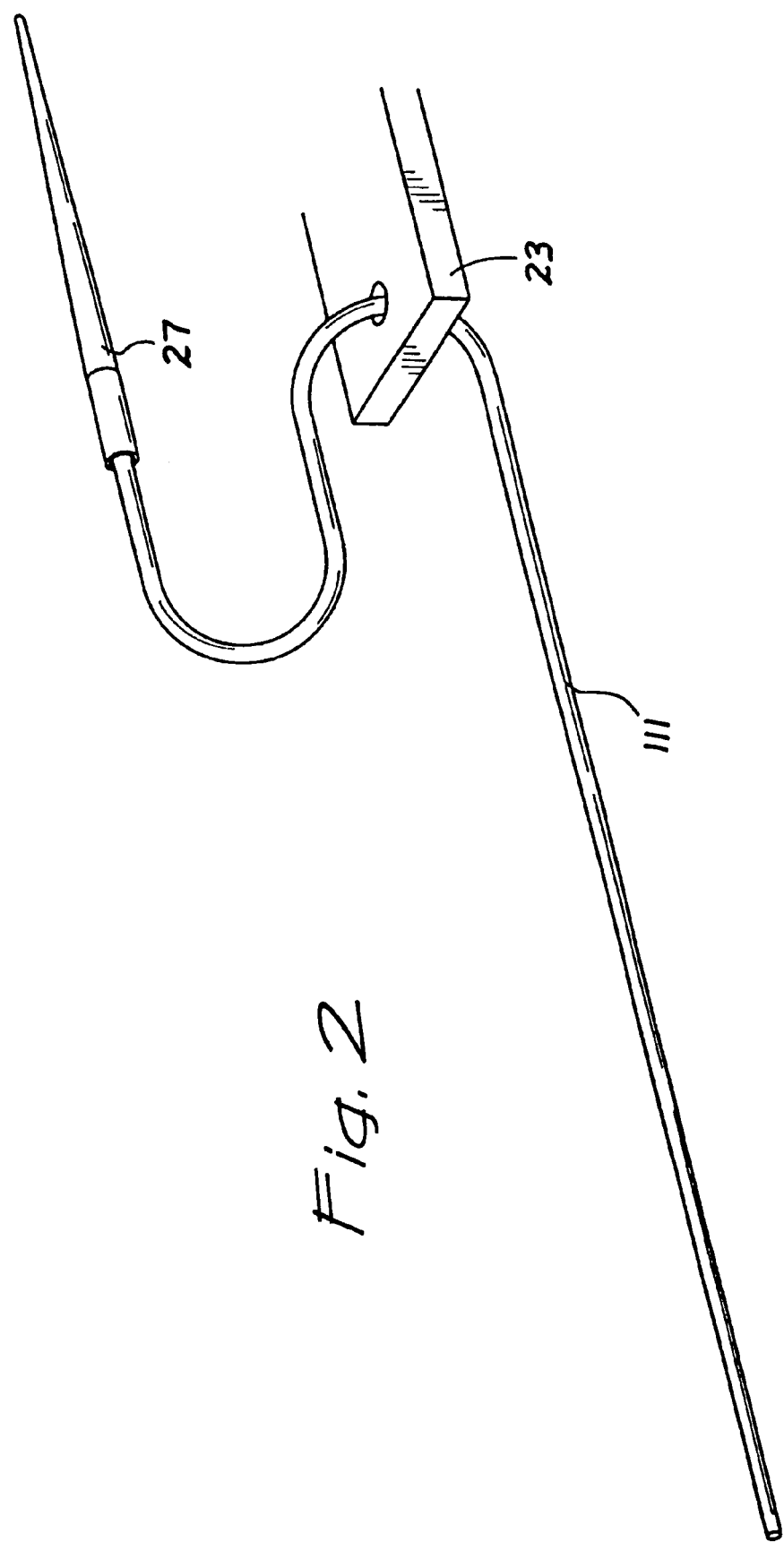

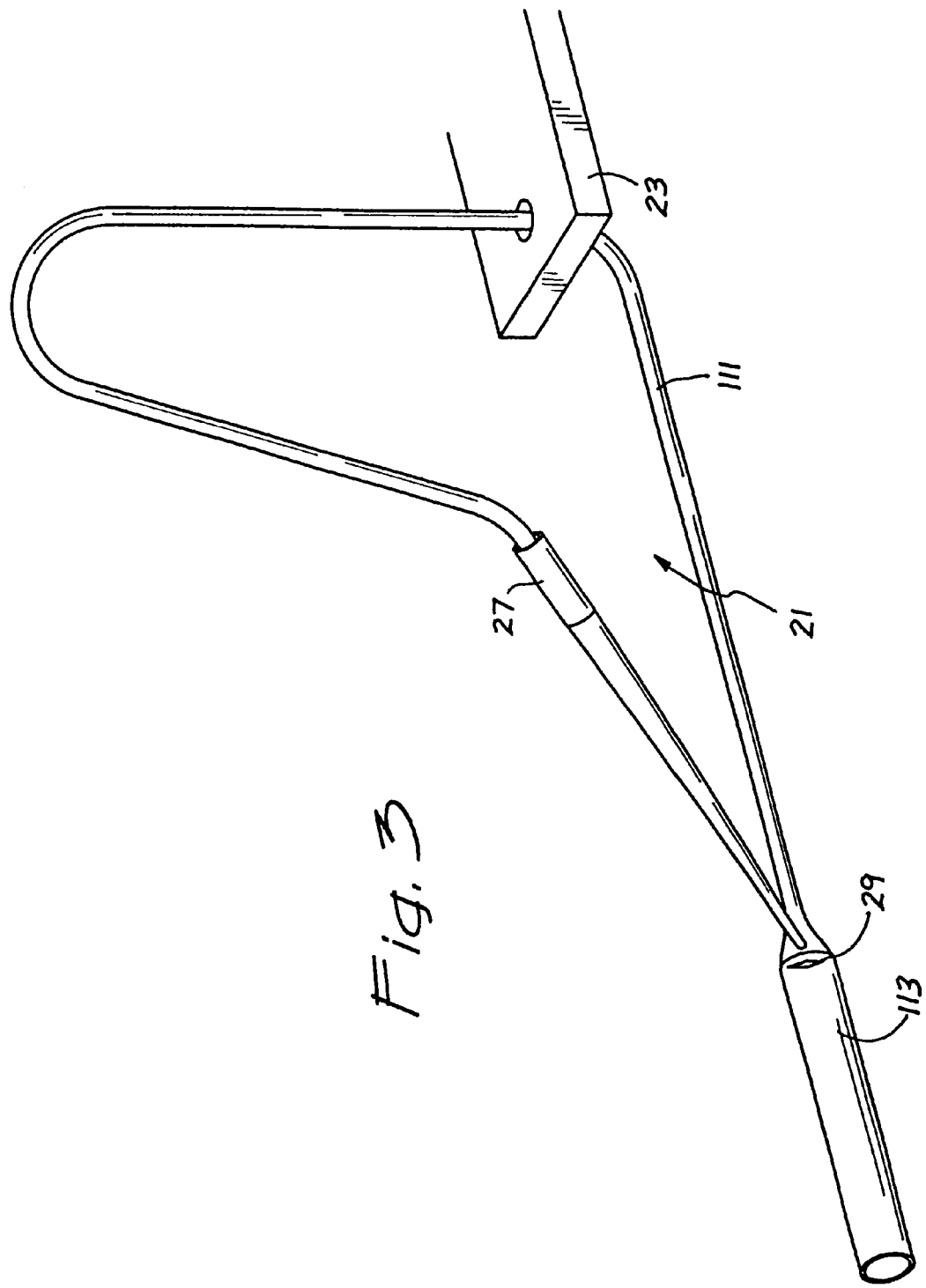

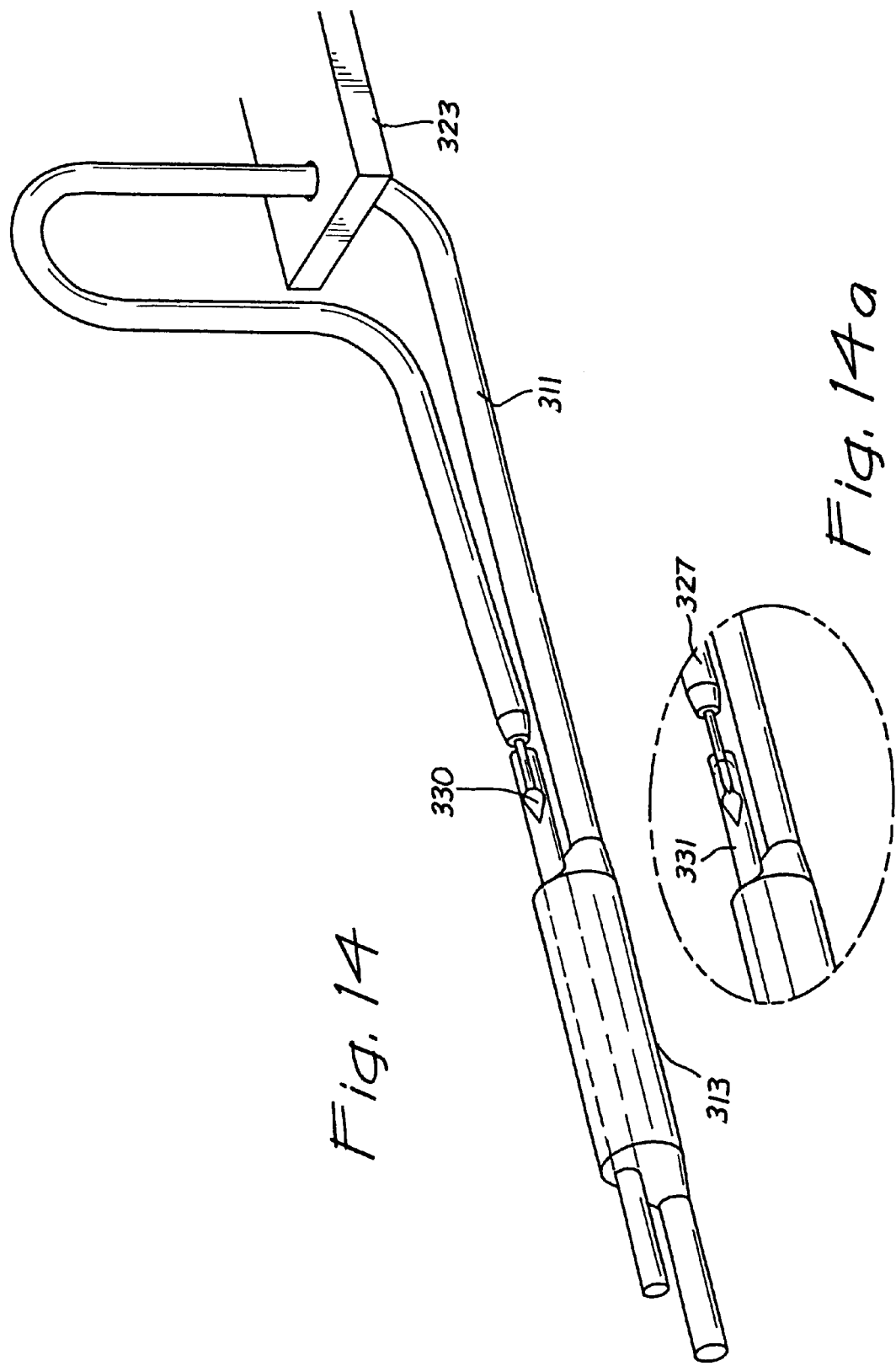

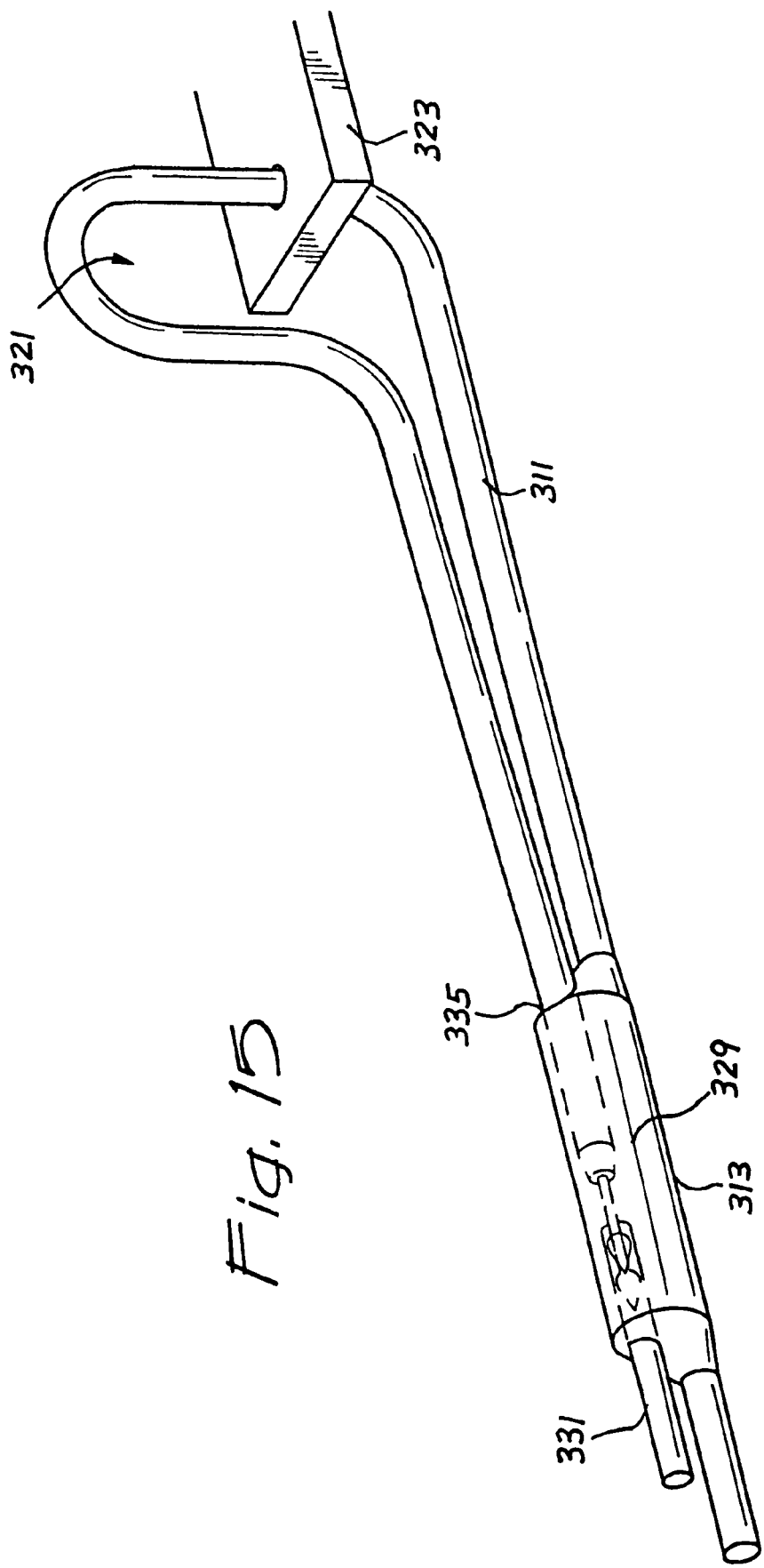

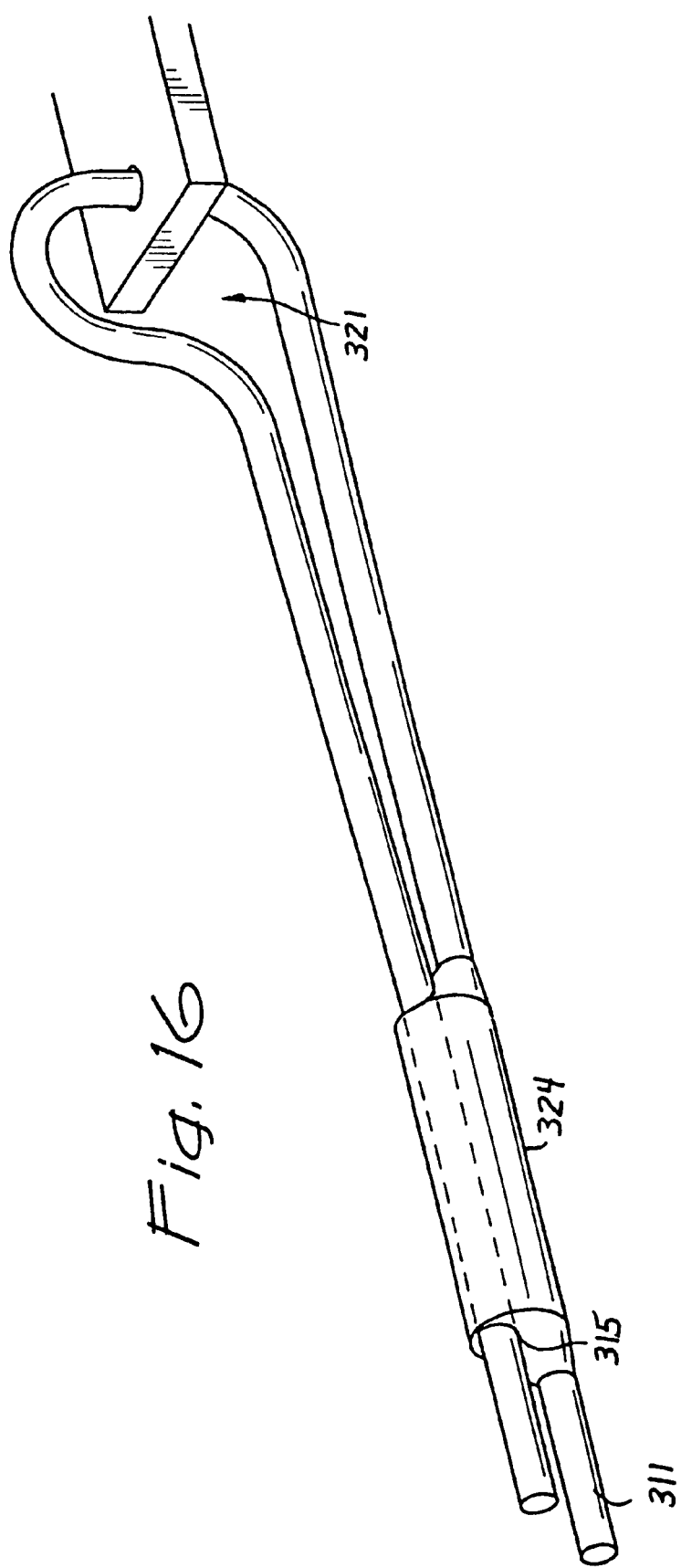

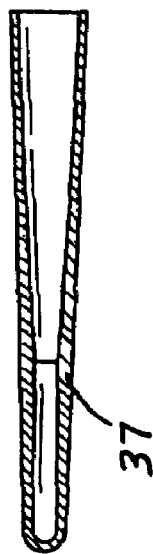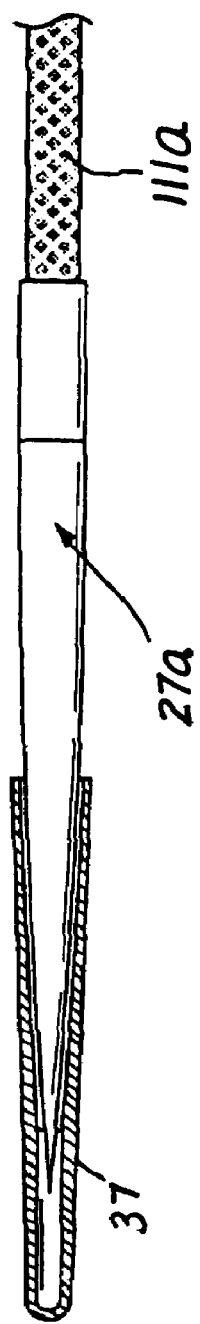

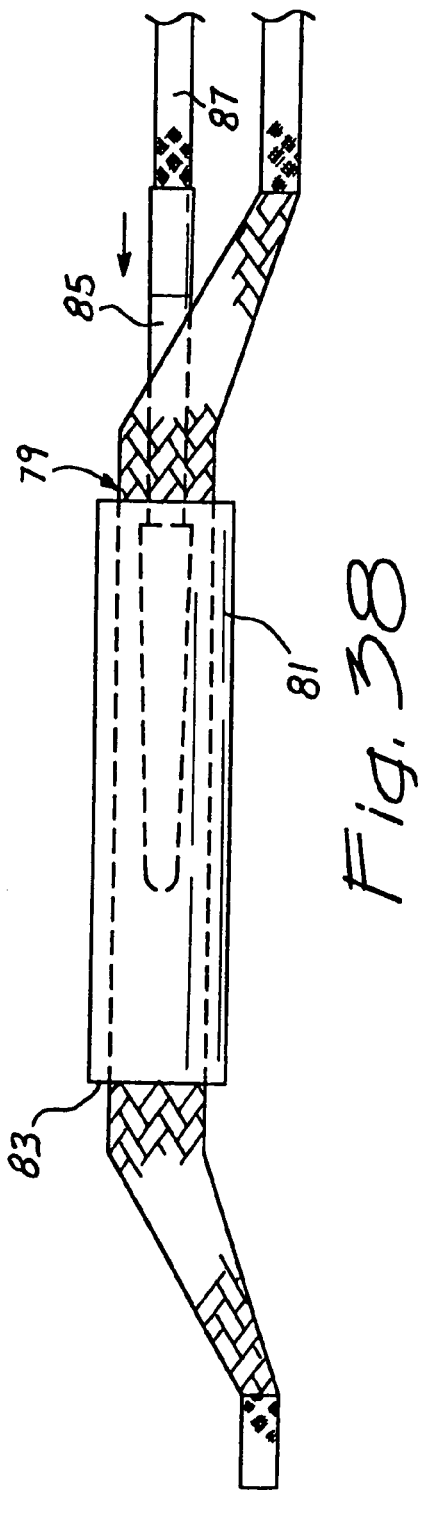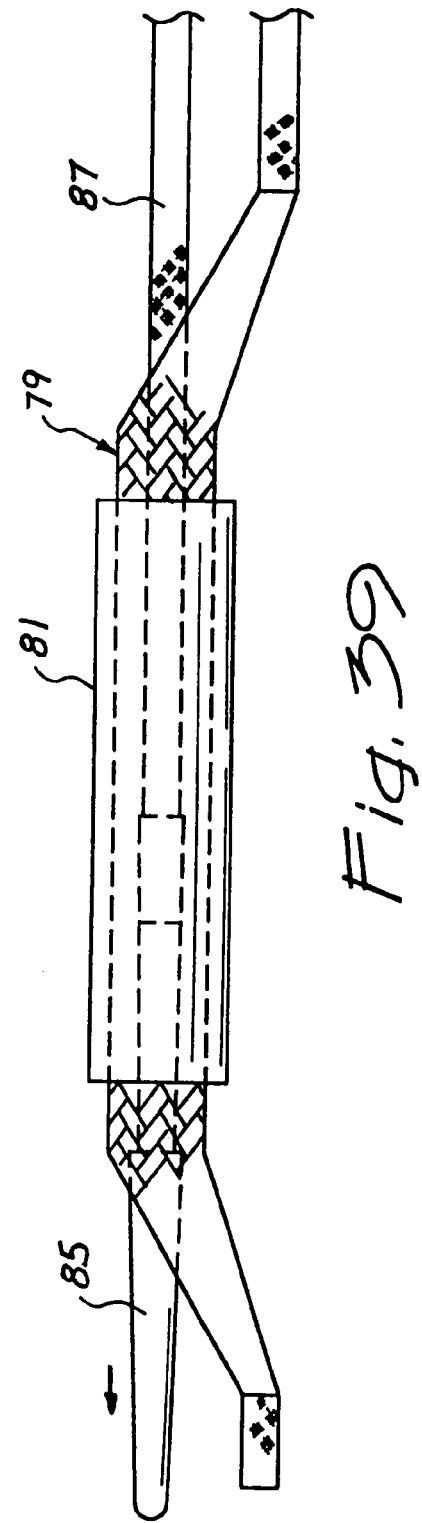
Fig. 38
Fig. 39

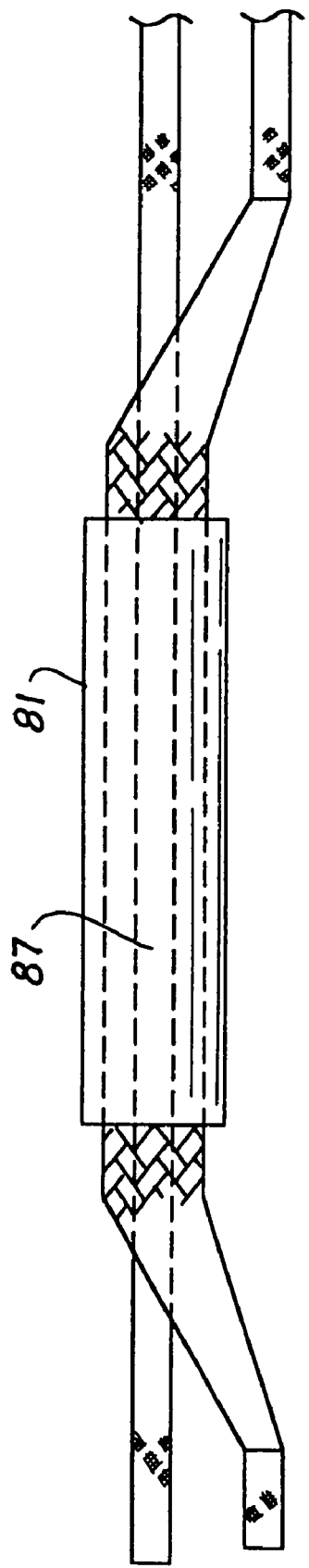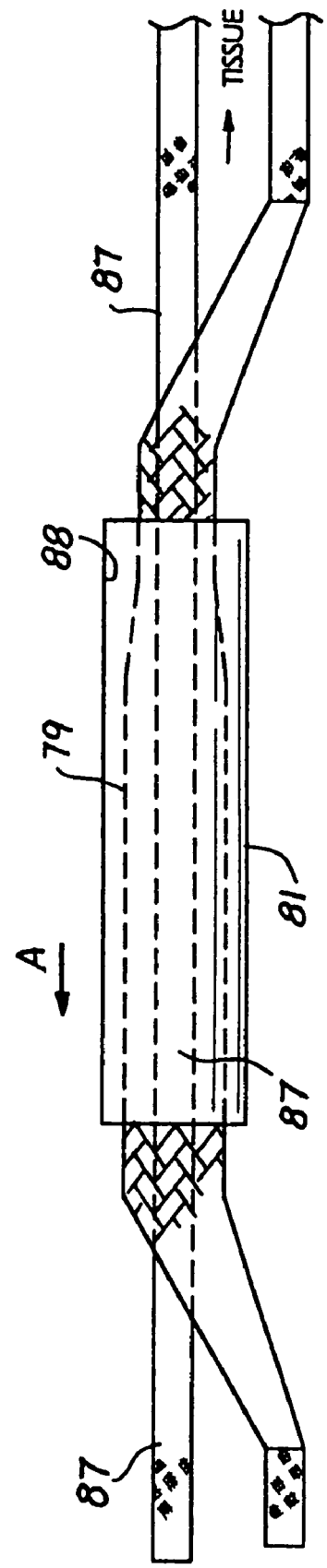

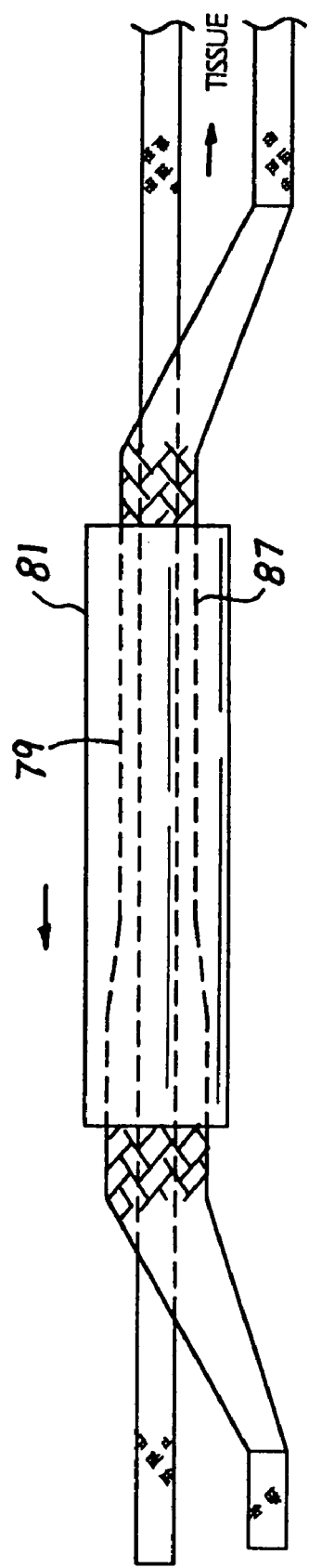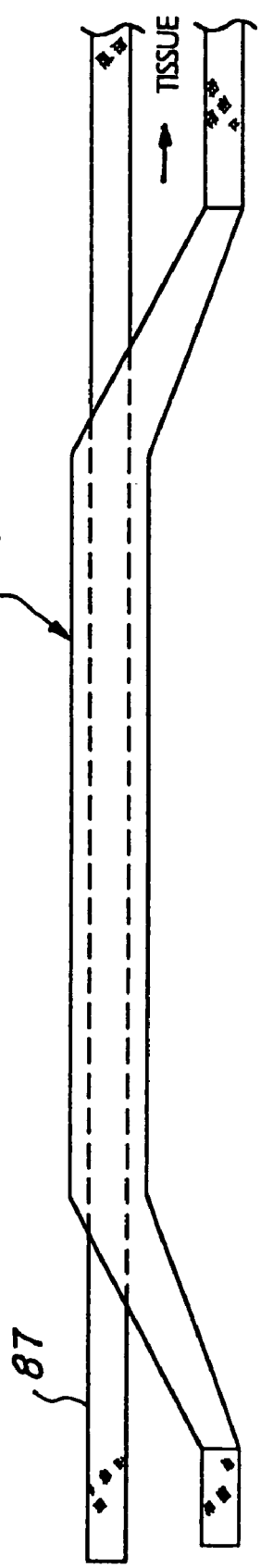

SINGLE-TAILED SUTURING METHOD

BACKGROUND OF THE INVENTION

This invention relates generally to the creation of a sliding and locking loop of cord, and more particularly to a surgical technique of suturing and the formation of a suture loop that may be tightened and locked.

Suturing is a necessary aspect of virtually any surgical procedure. Numerous techniques of tying sutures have been developed by surgeons over the years to address various applications of sutures. For example, a surgeon's knot, in which an overhand knot is modified to include two wraps of the suture ends around each other, was developed to minimize the amount of slippage in the suture as the second or locking throw of a ligation or approximation of tissue was accomplished. Another knot called a Roeder knot was developed to allow surgeons to place a loop of suture around a vessel for ligation in an endoscopic environment. The Roeder knot is basically a pre-tied slip knot that may be cinched and locked around a vessel or other structure. Many other knots, such as the Weston knot described in U.S. Pat. No. 5,405,352 address various other aspects of the surgical requirements of knots for flexibility, development of hoop stress (tightening of the suture loop), stability and reversibility.

In some cases, the development of a knot in a surgical procedure may require dexterity beyond the capability of the surgeon. This is certainly the case in surgeries such as arthroscopic, laparascopic, or thoroscopic surgery. These procedures are accomplished with the aid of an endoscope, a viewing instrument that can be used in conjunction with specialized surgical instrumentation to detect, diagnose, and repair areas of the body that were previously only able to be repaired using traditional "open" surgery. Access to the operative site using endosurgical or minimally invasive techniques is accomplished by inserting small tubes called trocars into a body cavity. These tubes have a diameter of, for example, between 3 mm and 30 mm and a length of about 150 mm (6 inches). A commonality in these procedures is that the spaces in which the surgeon works are limited, and the tools used for suturing make tying knots difficult at best. Surgeons are accustomed to handling the suture, as knots in open procedures are typically tied and pushed down to the wound using the fingers. In endoscopic procedures, either the knots need to be tied externally to the body and inserted into the body and to the operative site using some kind of knot pushing device, or they need to be tied inside the body using long, clumsy instruments.

Currently, in one known technique, the placement of sutures while using endoscopic techniques involves placing a semi-circular needle, attached to and carrying a suture, into a pair of endoscopic needle holders. These needle holders, which resemble a pair of pliers with an elongated shaft between the handles and the jaws, must be placed down through one of the surgical trocars into the body cavity containing the structure to be sutured. Because of their size, the needles used in these procedures are generally not able to be held in the jaws of the needle driver while being introduced through the operative trocar. The surgeon must hold the suture string in the needle holder jaws, and push the needle holder trailing the needle and suture into the body cavity. The suture and needle combination is dropped in the body cavity, and the needle is then located and picked up and properly positioned in the needle holder jaws. This is a difficult and time-consuming aspect of this current endoscopic technique for suturing. The needle carrying the suture may then be driven by pronation of the wrist, causing rotation of the elongate shaft, and subsequent arcuate rotation of the semi-circular needle.

The current instrumentation requires the surgeon to prepare the needle for penetration of the tissue while the needle is inside the body. This process is a time consuming, and sometimes frustrating exercise in hand to eye coordination, which is complicated by the fact that the surgeon is viewing the three dimensional space inside the body cavity through a two dimensional video monitor.

There have been other attempts to improve the methods of tissue repair. These include the development of staplers and anchoring devices. In response to some of the aforementioned problems in placing sutures in tissues endoscopically, manufacturers have developed tissue staplers. These devices utilize stainless steel or titanium staples that are constructed much like the staples used to hold papers together. The major disadvantage of these kinds of staplers is that they leave metal in the body. For some tissues this is not a problem, however in some procedures, metal staples left within the tissues can be a major hindrance to the healing process.

In orthopedic surgery, many different designs for bone anchors have been developed. These anchors allow soft tissues to be reattached to bone, and simplify the process by removing the need to create a transosseous tunnel. Transosseous tunnels are created in bones to allow suture material to be threaded through and tied across the bony bridge created by tunnels after the suture material has been placed through the soft tissues and tied with conventional knots. Anchors are commonly used in joint re-constructions, and because the metal is contained in the bone, it does not cause a problem with healing.

While endoscopy has certainly found favor with many physicians as an alternative operative modality, the advanced skill set and operative time necessary to become an efficient and practiced endoscopist have proven to be a challenge for a large portion of the surgical community. The cost pressures brought about by large scale patient management (the continued rise and success of health maintenance organizations or HMO's) have also caused the surgical community to cast a critical eye on the overall costs and long-term outcomes of some of the procedures that have been tried via a endoscopic approach. While the laparascopic cholecystectomy (gall bladder removal) has certainly proven its worth in the past 8–10 years, many other procedures have not shown similar cost effectiveness and positive long-term outcomes.

Hence, alternatives have been sought to bridge the gap between skill and equipment intensive endoscopic surgery and more familiar open surgery. As such, under the broad umbrella of "minimally invasive surgery" which would include endoscopic surgery, a relatively new approach called "mini-incision surgery" has begun to emerge. This approach uses the principles of traditional open surgery, along with some of the equipment advances of endoscopy to provide the patient with the best of both worlds.

Perhaps the most visible of these new approaches is the emergence of minimally invasive heart surgery, both for coronary bypass and for valve replacement. Techniques and tools for cardiovascular surgery have begun to be used that allow the heart surgeon to perform procedures through small incisions between the ribs that previously required a massive incision and splitting the sternum to gain access to the heart.

In a similar way, orthopedic surgeons have begun to explore alternatives to the traditional open approach for the many indications requiring reconstruction of some aspect of the shoulder. As was the case when minimally invasive approaches were adopted for knee repair and re-construction, the use of either an endoscope or a "mini-open" approach is gaining in popularity with surgeons, patients and third party payers.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The "classic open" approach requires a large incision and complete detachment of the deltoid muscle from the acromion to facilitate exposure. Following the suturing of the rotator cuff to the humeral head, the detached deltoid is surgically reattached. Because of this maneuver, the deltoid requires postoperative protection, thus retarding rehabilitation and possibly resulting in residual weakness. Complete rehabilitation takes approximately 9 to 12 months.

The "mini-open" technique, which represents the current growing trend and the majority of all surgical repair procedures, differs from the classic approach by gaining access through a smaller incision and splitting rather than detaching the deltoid. Additionally, this procedure is typically used in conjunction with arthroscopic acromial decompression. Once the deltoid is split, it is retracted to expose the rotator cuff tear. The cuff is debrided to ensure suture attachment to viable tissue and to create a reasonable edge approximation. In addition, the humeral head is abraded or notched at the proposed "soft tissue to bone" reattachment point, as healing is enhanced on a raw bone surface. A series of small diameter holes, referred to as transosseous tunnels, are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion.

Although the above described surgical technique is the current standard of care for rotator cuff repair, it is associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

However, as will now be described, there are cases where the knots themselves are a hindrance to the healing of the wound. In cases where joint re-constructions are undertaken by orthopedic surgeons, oftentimes the space available within joint is quite limited. This is especially true, for example, in a rotator cuff repair. The knots in the tendon can be bulky and create a painful impingement of the tendon on the bone. Because non-absorbable suture materials are used for these types of repairs, the suture and associated knots are not absorbed into the body, and hence provide a constant, painful reminder of their presence. It would therefore be desirable to develop a system that did not require the traditional knots to secure the suture to the tendon.

So it may be seen that none of the currently extant approaches to the placement and securing of sutures in, for example, rotator cuff surgery have fulfilled all of the surgeon's requirements.

What is needed, therefore, is a new approach for repairing the rotator cuff, wherein suture tension can be measured and adjusted, the suture resides completely below the cortical bone surface, there is no requirement for the surgeon to tie a knot to attach the suture to the bone anchor, and the skill level for correct placement is suitable for practitioners having average ability.

SUMMARY OF THE INVENTION

Accordingly, the inventors have developed a novel system and method for creating a suture loop and securing the suture material to tissue. This is done by taking advantage of some of the unique aspects of the construction of braided sutures. These sutures, commonly constructed out of silk, cotton, or polyester fibers, are woven into an 8 to 10 ply hollow diamond braid. Oftentimes, one or two core fibers are run down the middle of the diamond braid. In the present invention, these core fibers are eliminated. They may be replaced by pull loops, which will be more fully explained below.

The hollow nature of the diamond braid allows for the formation of a unique "single-tailed" suture. This suture is formed by taking one end of the suture (the free end) and passing it through an opening formed in the diamond braid and into the hollow interior lumen of the other half of the suture (the standing part). Much like the familiar children's toy which is commonly identified as a "Chinese finger torture", the diamond braid, by the very nature of its configuration, is able to expand and contract in diameter based on the forces exerted on the fibers. When the suture or hollow core cord is placed in compression, the fibers allow for the expansion of the diameter, both exteriorly and in the hollow inner lumen. When tension is placed on the suture, the fibers are allowed to contract, and, in the case of the single tailed suture, the free end that has been passed into the interior lumen of the standing end is compressed and held by the contraction of the diameter of the standing part.

There are many different methods and tools that can be used to create the single tail loop. In the present invention, various configurations of fids, pull strings, and other tools may be used to thread the free end of the suture through the interior lumen of the standing end of the suture. A fid is a tool that allows the free end to be threaded through the standing end by parting the fibers of the hollow cord wall. A fid is typically a hollow, tapered cylinder with a smoothly closed end and an open end that is disposed to receive the free end of the hollow cord. It has an outside diameter minimally greater than the outside diameter of the cord.

More particularly, there is provided a suture having a structure which comprises a plurality of flexible filaments loosely woven together in a tubular geometry. The desired tubular geometry includes an outer wall which defines an internal lumen. The construction is such that when a first portion of the suture is placed under compression, the outer wall of the first portion is radially expanded, such that a diameter of the first portion internal lumen increases in size sufficiently so that a second portion of the suture structure, which is not under compression, may be accommodated within the first portion lumen. However, when the suture first portion is subsequently placed under tension, while the suture second portion is disposed within the first portion lumen, the diameter of the first portion lumen decreases sufficiently to capture the suture second portion therein to create a binding interface between the first and second suture portions, thereby locking the second suture portion in axial position within the lumen of the first suture portion.

In another aspect of the invention, a single-tailed suture is disclosed for securing a plurality of body components together. The inventive single-tailed suture comprises a length of braided suturing material having a distal portion and a proximal portion, and a braided outer wall which defines an internal lumen, wherein the braided suturing material extends through one of the body components, such as a tendon. A distal end of the braided suturing material extends through the outer wall of the proximal portion so that a predetermined length of the distal suture portion is disposed within the lumen of a predetermined length of the proximal suture portion. The predetermined length of the proximal suture portion is in tension to create a binding interface between the predetermined length of the distal suture portion and the predetermined length of the proximal suture portion to create a suture loop.

In yet another aspect of the invention, a method of suturing a plurality of body components together is described, wherein the inventive method uses a length of braided suturing material which comprises a plurality of flexible filaments loosely woven together in a tubular geometry comprising an outer wall which defines an internal lumen. A first step in the inventive method is to insert a distal end of the suturing material through a portion of a first one of the body components, wherein the body components may comprise soft connective tissues such as tendons or ligaments, and/or bone. Then, a predetermined length of a portion of the braided suturing material which is proximal to the first body component is compressed, so that an internal diameter of the lumen of the compressed suture portion increases substantially in size. At this juncture, a distal end of the length of braided suturing material is inserted through the outer wall of the compressed suture portion and into the internal lumen thereof, so that a desired length of the braided suturing material which is distal to the first body component is disposed within the internal lumen of the compressed suture portion.

Once the foregoing steps have been performed, and the compressed suture portion is moved to a desired point, so that the resultant suture loop will be of a preferred size, tension is applied to the compressed suture portion to decrease the internal diameter of its lumen, to thereby create a binding interface between the compressed suture portion and the suturing material disposed in its lumen, so that the aforementioned suture loop of a desired length is formed.

The invention, together with additional features and advantages thereof, may best be understood by reference to the following description taken in conjunction with the accompanying illustrative drawing.

BRIEF DESCRIPTION OF THE DRAWINGS

FIG. 1a is a schematic view illustrating a basic construction of hollow cords or sutures of the type utilized in the present invention, in tension;

FIG. 1c is a schematic view similar to FIGS. 1a and 1b, illustrating the creation of a binding interface between two portions of a hollow suture which is of a construction like that shown in FIGS. 1a and 1b, wherein one of the suture portions is disposed within the internal lumen of the other of the suture portions;

FIG. 1d is an end view of the hollow suture illustrated in FIG. 1a;

FIG. 1f is an end view of the hollow suture binding interface illustrated in FIG. 1c;

FIGS. 2 through 7 are schematic perspective views illustrating in sequence an apparatus and method for forming a single tail suture in accordance with the present invention;

FIGS. 13 through 16 are schematic perspective views illustrating in sequence still another alternate apparatus and method for forming a single tail suture in accordance with the present invention;

FIGS. 17a through 17c are detail plan views of a fid, a suture needle, and an adaptation of a suture needle to a fid, respectively;

FIG. 18 is a detail perspective view illustrating the fid combination of FIG. 17c as it is being inserted through the outer wall 118 of a suture 113a;

FIGS. 38 through 40 are plan views, in sequence, illustrating yet another alternative embodiment and method for creating and tensioning a single tail suture; and FIGS. 41 through 43 are plan views similar to those of FIGS. 38 through 40, illustrating, in sequence, a method by which the expanded braid of FIGS. 38–40 may be tensioned over the suture.

DESCRIPTION OF THE PREFERRED EMBODIMENT

Figure 1B:
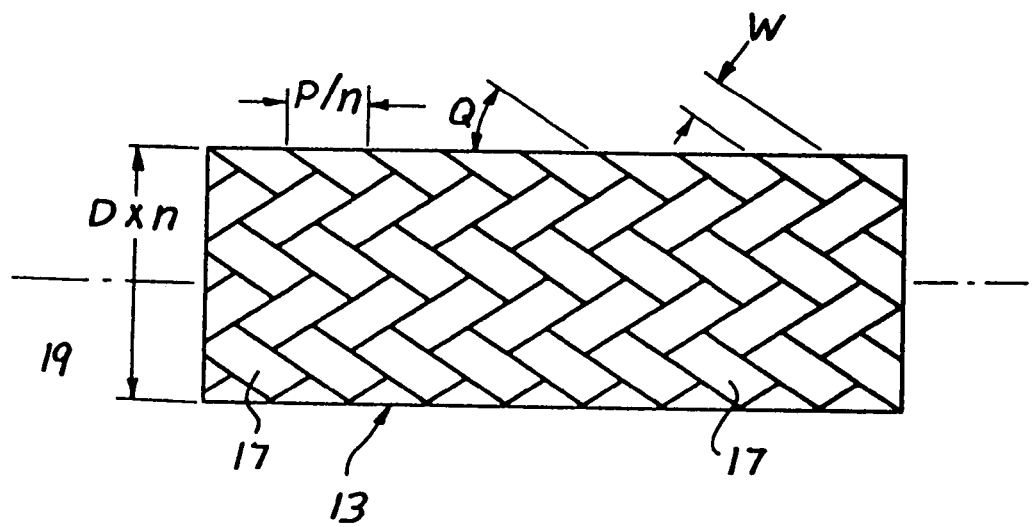
FIG. 1b is a schematic view similar to FIG. 1a, illustrating the hollow suture of FIG. 1a in compression, rather than tension.
Figure 1E:
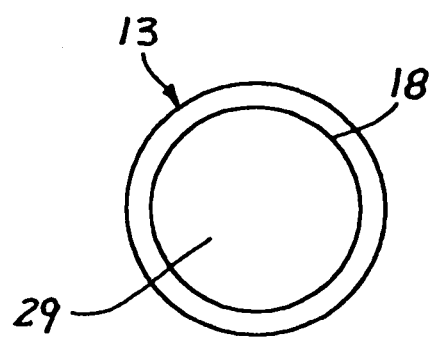
FIG. 1e is an end view of the hollow suture illustrated in FIG. 1b.

Referring now more particularly to the drawings, FIG. 1a shows a tensioned suture 11 of a braided construction, in tension. The tension on the suture preferably sets characteristics of the suture so that it is of diameter D and pitch P. FIG. 1b shows the tensioned suture 11 loaded with axial compression to form a compressed suture 13, the suture braid being designed so that its pitch and diameter are affected by the axial compression on the suture by a factor "n" as shown. The factor "n" is of such a value that it makes possible the passage of the tensioned suture 11, having the diameter D, through the center of the compressed suture 13. The factor "n" is also of such a value that the interior of compressed suture 13 further provides for the passage of any instrument that is required for the manipulation of the suture.

In a preferred configuration, the factor "n" ranges in value from a minimum of about 1.5 to a maximum of about 15.0 in order to achieve acceptable performance, with a range of about 2 to 4 being preferred.

When the tensioned suture 11 is passed through the compressed suture 13 and the compressed suture 13 is further manipulated to be tensioned about the tensioned suture 11, there is created a binding interface 15 of a length L between the tensioned suture 11 and the compressed suture 13 as shown in FIG 1c. As will be shown, the nature of the binding interface 15 is related directly to the tension in compressed suture 13, the length L (which is approximately equal to the length of the formerly compressed suture 13), and to an interface frictional factor. The nature of the binding interface 15 is further directly related to the value of an angle "Q", which is defined as the angle of orientation of fibers 17 which form the braided outer cylindrical wall 18 of the suture 11,13, relative to a longitudinal axis 19 of the compressed suture 13, as shown in FIG. 1b. More particularly, the nature of the binding interface is related to the sine of angle Q. An important aspect of the present invention is the inventors' discovery of the ability to define and control the degree of binding interface between the sutures 11 and 13, thereby providing a controllable means of binding and securing sutures in tissue. In FIG. 1c, the binding interface 15 extends along a bound portion 24 of the suture, which is approximately co-extensive with the length along which the tensioned suture 11 extends within the interior of the (formerly) compressed suture portion 13.

It is to be understood that hollow braided cord such as the suture 11 described supra is constructed using a number of separate fiber bundles ("picks") which are woven together to form a braid. There is always an even number of bundles, as an equal number of bundles are woven in each direction. A typical number of bundles is 12, with 6 woven clockwise, and 6 woven counterclockwise. For the purposes of understanding the relationship between the tension in the suture and the binding force, we will consider a single bundle, with the assumption that each bundle is subjected to the same forces and acts in a similar way within the structure of the hollow braided cord.

Considering a single fiber bundle 17 (FIG. 1b), it is seen that the geometry described by that bundle within the braided cord is roughly helical, with deviations from a perfect helix to accommodate the over and under construction of braiding. For purposes of modeling the forces on the single fiber bundle 17, we will consider a single revolution of the bundle and smooth the bundle to a consistent helix, recognizing that the forces on the bundle are consistent throughout the strand and along the length of the suture.

For ease of reference, the variables used in the following derivation are listed below:

T—Tension in the hollow cord or suture
Q—Angle formed by a single fiber bundle to the centerline of the hollow cord
r—Radius of the thin-walled cylinder approximating the hollow cord
t—Wall thickness of the thin-walled cylinder
L—Length of the hollow cord
S—Stress
b—Total number of fiber bundles in the hollow cord
w—width of a single fiber bundle
N—Normal force developed by a single fiber bundle
p—Pressure generated by tension in the hollow cord
$F_f$—Force generated by a single fiber bundle
$F_t$—Total force generated by all of the fiber bundles b Now, the binding interface is a frictional force developed as a result of the normal force N exerted by the outer suture on the inner suture. The normal force N is equal to the pressure or hoop stress developed, multiplied by the area. The tension T in the suture creates a pressure which is a function of the angle Q formed by the single bundle 17 to the centerline 19 of the hollow cord. It may be understood that, as the angle Q approaches zero, the induced pressure approaches zero. For purposes of calculation, the hollow cord may be mathematically approximated as a thin-walled cylinder of radius r, wall thickness t, and length L. Stress, represented by S, for thin-walled cylinders is represented by the equation:

$$t = \frac{pr}{S} \tag{1}$$

(from page 325, *Mechanics of Materials*, Beer and Johnston, McGraw-Hill Book Company, 1981), which, solving for stress S yields:

$$S = \frac{pr}{t} \tag{2}$$

The component of the force developed by the tension T in the cord which is normal to the centerline of the cord is expressed as:

$$T \cdot \sin Q \tag{3}$$

We can equate the stress S in the cord to the force per unit area developed by the tension T in the cord, where the area A is defined by the thickness t multiplied by the width w of a single fiber bundle. Now the total tension T is distributed throughout all of the fiber bundles b, and so the tension in a single fiber bundle is:

$$\frac{T}{b} \tag{4}$$

Therefore, we see:

$$S = \frac{pr}{t} = \frac{T\sin Q}{btw} \quad (5)$$

and, solving for p, we get:

$$p = \frac{T\sin Q}{bwr} \quad (6)$$

Now, the normal force generated by this pressure is the pressure times the unit area, with the area being equal to the circumference of the cylinder times the width, or:

$$N = pA = \frac{w2\pi r T\sin Q}{bwr} \quad (7)$$

and simplifying, we get:

$$N = 2\pi \frac{T}{b}\sin Q \quad (8)$$

As will be understood by those skilled in the art, frictional force is equal to the normal force multiplied by a friction coefficient, normally represented by $\mu$. The equation then becomes:

$$F_f = \mu N = 2\mu\pi T \sin Q \quad (9)$$

The total force developed over all of the fiber bundles b of the hollow cord with a length L and a number of fiber bundles or picks per inch of k then becomes:

$$F_t = \frac{2kL\mu\pi T\sin Q}{b^2} \quad (10)$$

It may be seen from this equation that in order for the single-tail suture of the present invention to lock, F must be larger than T, and therefore the constant $$\frac{2kL\mu\pi\sin Q}{b^2}$$

must be larger than one.

Now, the frictional coefficient $\mu$ is simply a material property, and k (picks per inch), L (length), Q (angle between the centerline and the pick), and b (total number of picks) are design parameters. It may be seen, therefore, that by judicious selection of the constants k, L, Q, and b, a self-locking system may be developed that optimizes the bound interface.

Figure 4:
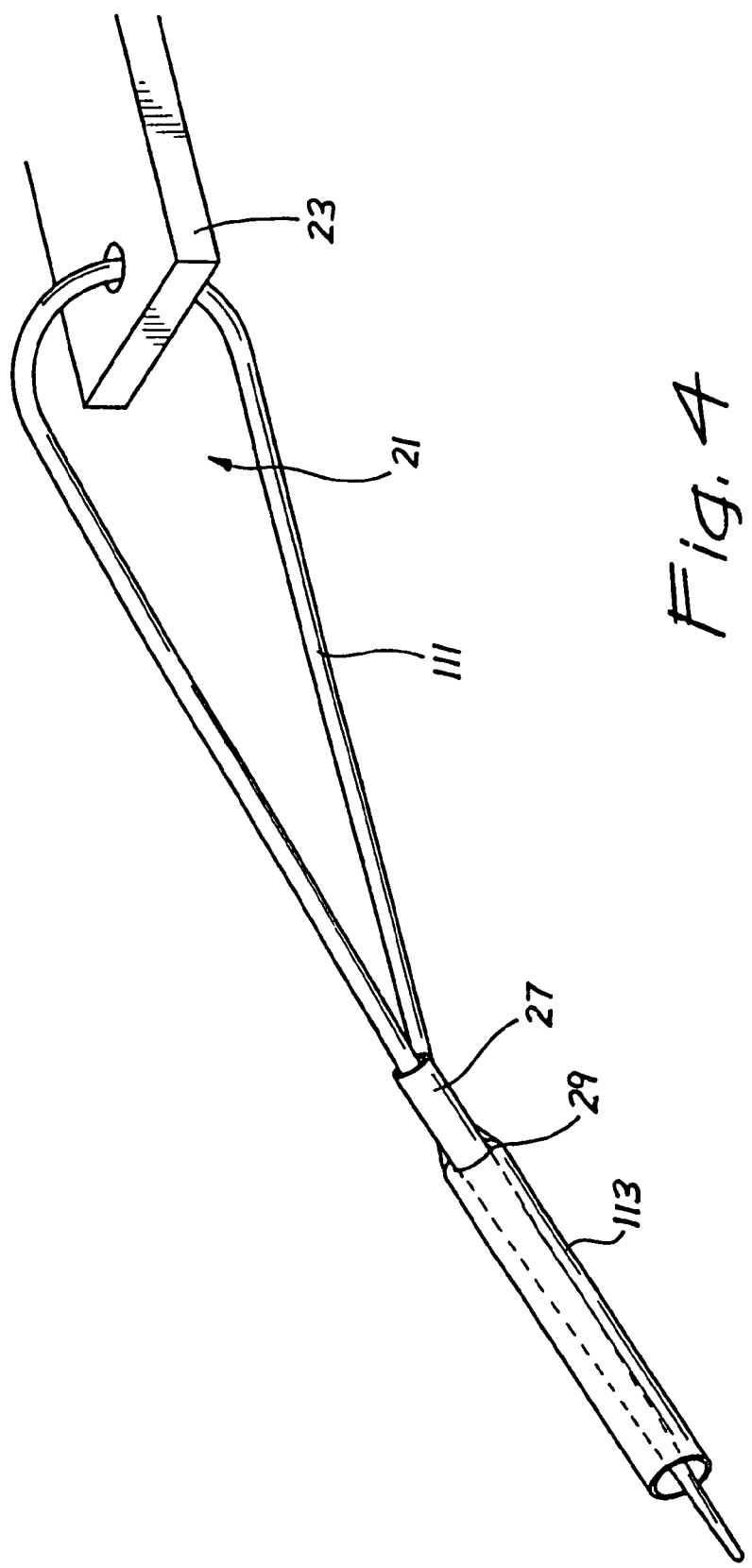
Figure 5:
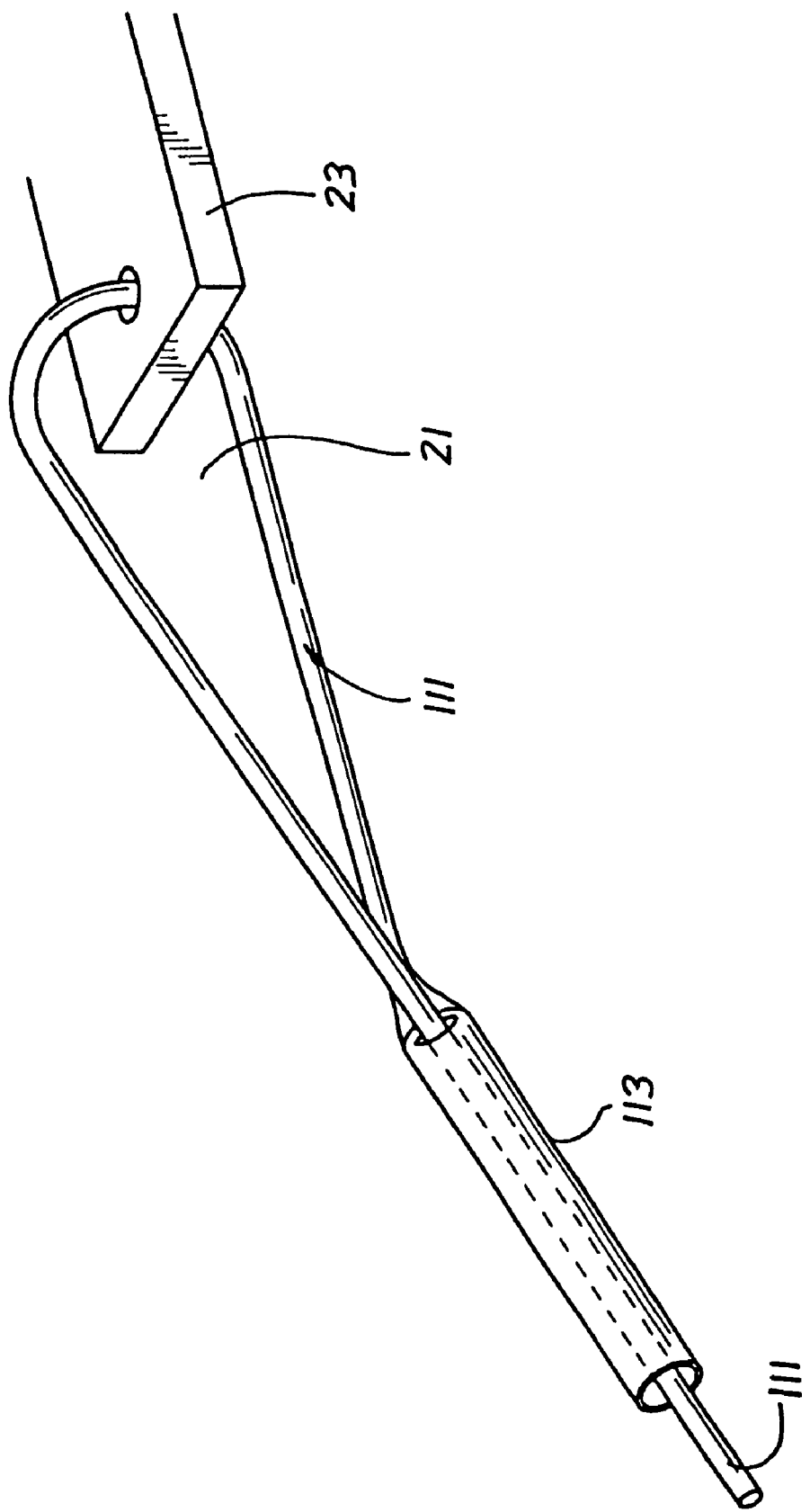
Figure 6:
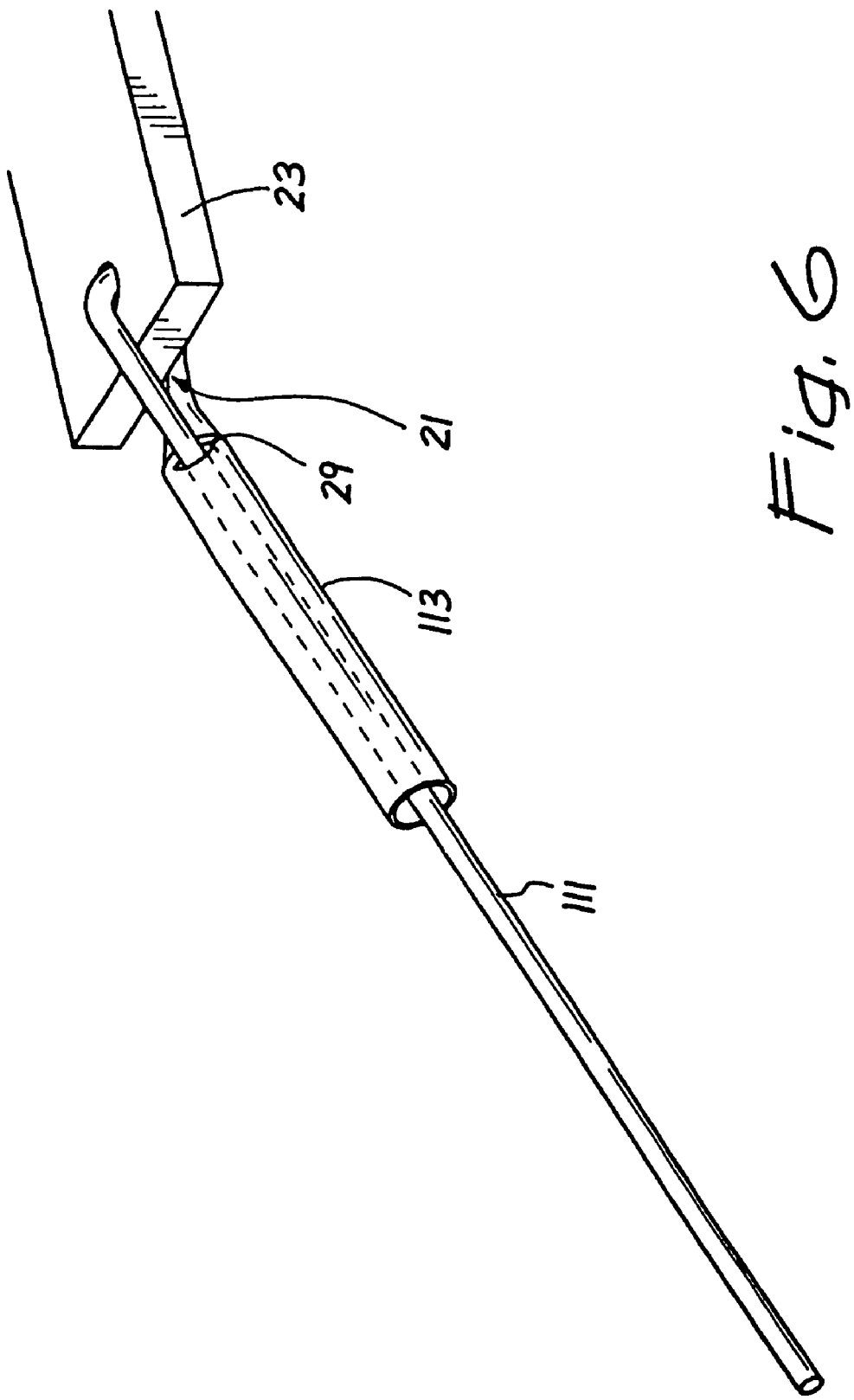

Now with particular reference to FIGS. 2–7, wherein like or functionally equivalent elements to those illustrated in prior embodiments are designated by like reference numerals, preceded by the numeral 1, there is illustrated one preferred embodiment of this bound interface which will serve to attach a suture loop 21 (FIGS. 3–7) to one piece of tissue 23. Suturing material 111, forming the suture loop 21, is of a braided construction which will allow a needle or fid 27 to pass through the center of the compressed portion 113 of the braided suture 111 when it is in compression. The fid 27 may be passed through the tissue 23 by common instruments of the art. Referring to FIG. 3, the compressed portion 113 is created by manipulation of the braided sheath (typically the practitioner's fingers are used to "bunch" the fibers 117 forming the braided sheath together in compression along a portion of the length of the suture 111) and access to an interior lumen 29 is identified. The fid 27 is then inserted into the interior lumen 29, as shown in FIG. 4. Once inserted, the fid 27 is drawn out of the end of the compressed portion 113 and optionally clipped off, as shown in FIG. 5. The compressed portion 113 is then pushed, sliding it along the tensioned suture 111 to create the desired suture loop 21 geometry, as shown in FIG. 6. Of course, as will be appreciated, the compressed portion 113 is literally merely a portion of the tensioned suture 111 which has been manipulated into a compressed (or "bunched") state. Thus, it is not literally "pushed". Rather, by sliding one's fingers or another suitable instrument along the length of the tensioned suture 111, behind the compressed portion 113, one can "move" the compressed portion 113 along the length of the suture 111 (literally changing the portion of the length of the suture 111 which is in compression, in the manner similar to that of a standing wave).

Figure 7:
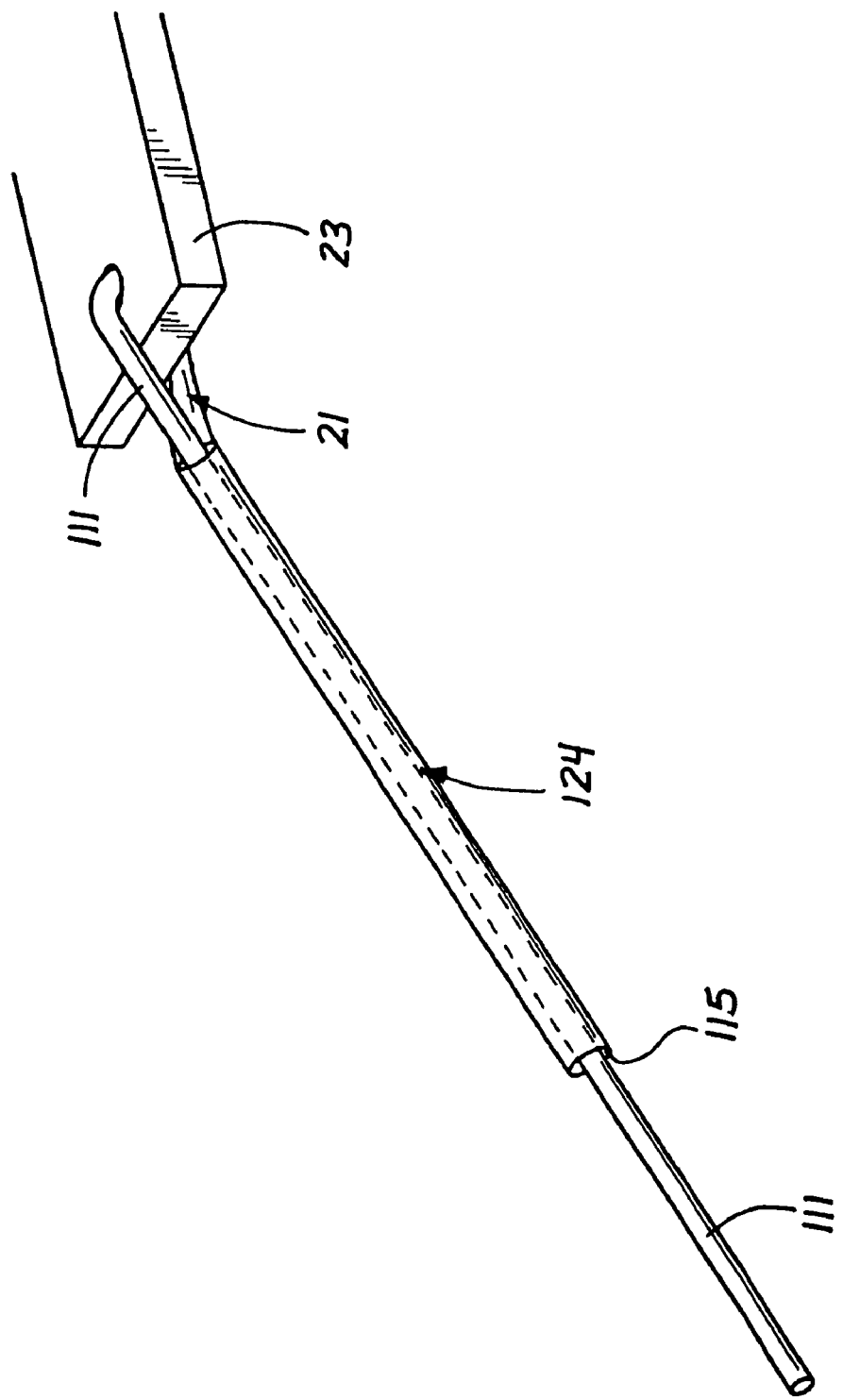

Once the desired suture loop 21 geometry has been achieved, it can be "locked" into place by applying tension on the compressed portion 113, as shown in FIG. 7, until the interior lumen 29 thereof decreases in diameter sufficiently to engage the portion of tensioned suturing material 111 which is disposed therein. This creates a binding interface 115 between portions 113 and 111 of the suture, the binding interface 115 being designed in length and pitch of braid to provide a bound end 124 to the suture loop 21 when suture 21 is in tension.

Figure 8:
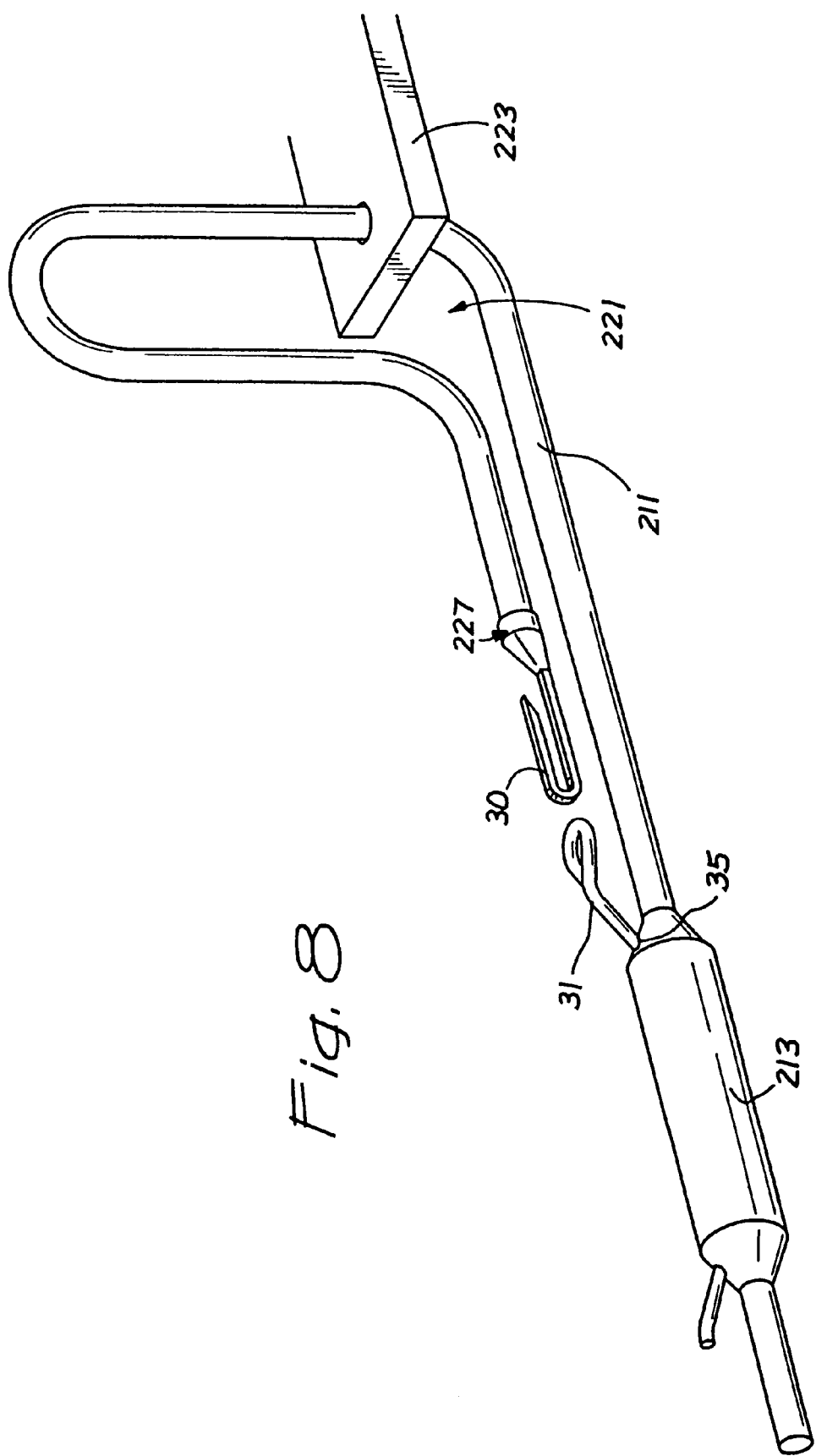
FIGS. 8 through 12 are schematic perspective views similar to FIGS. 2 through 7, illustrating in sequence an alternate apparatus and method for forming a single tail suture in accordance with the present invention.
Figure 9:
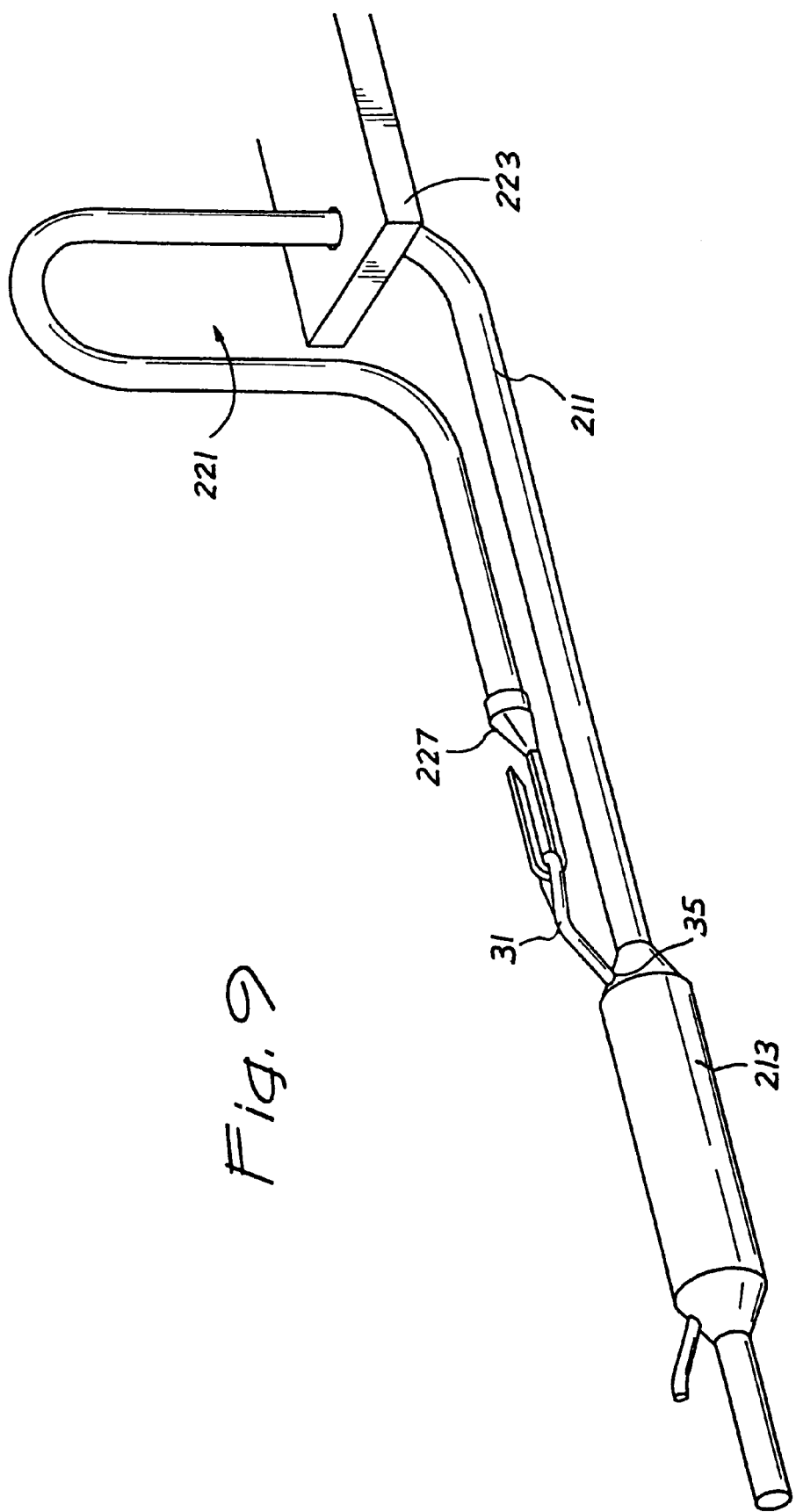
Figure 10:
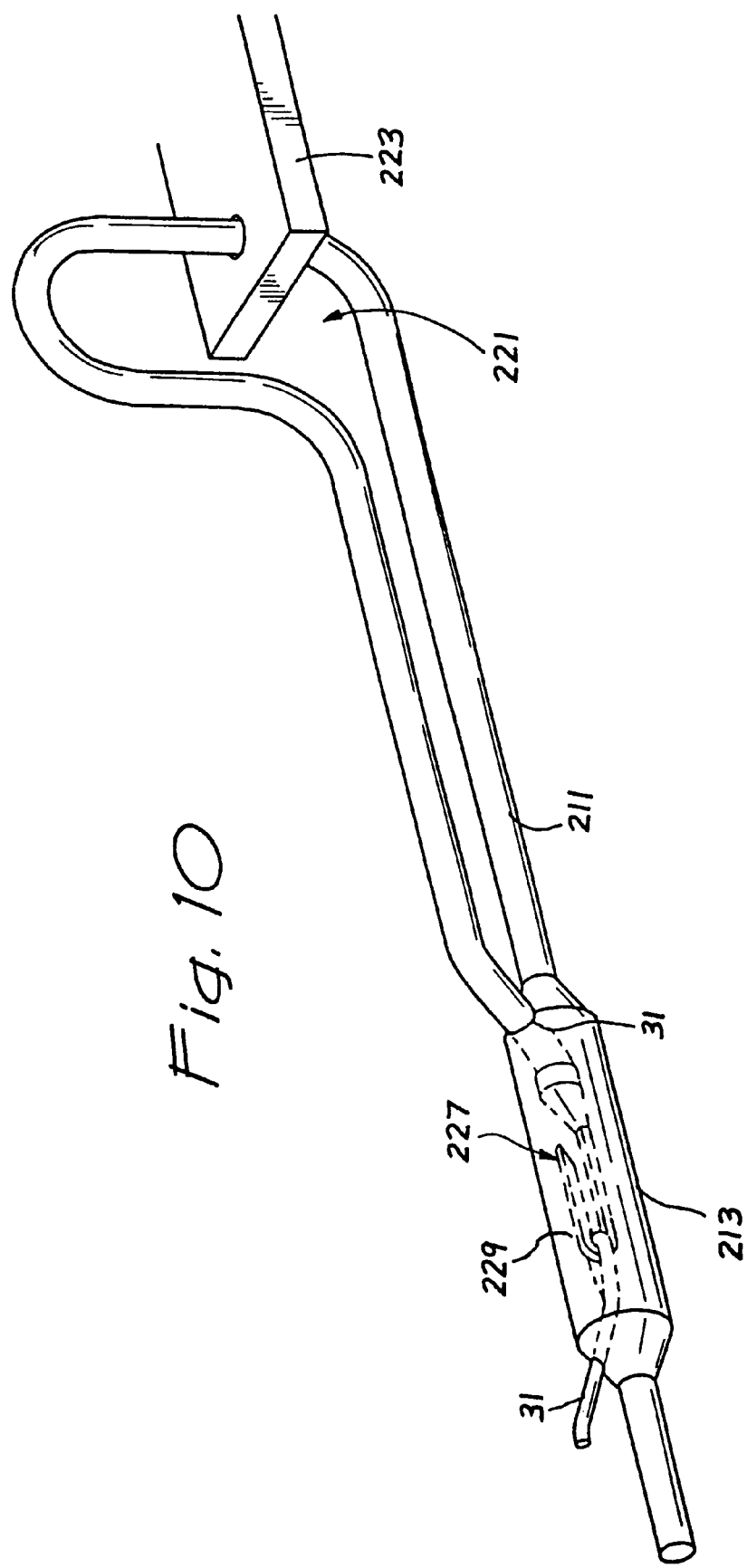
Figure 11:
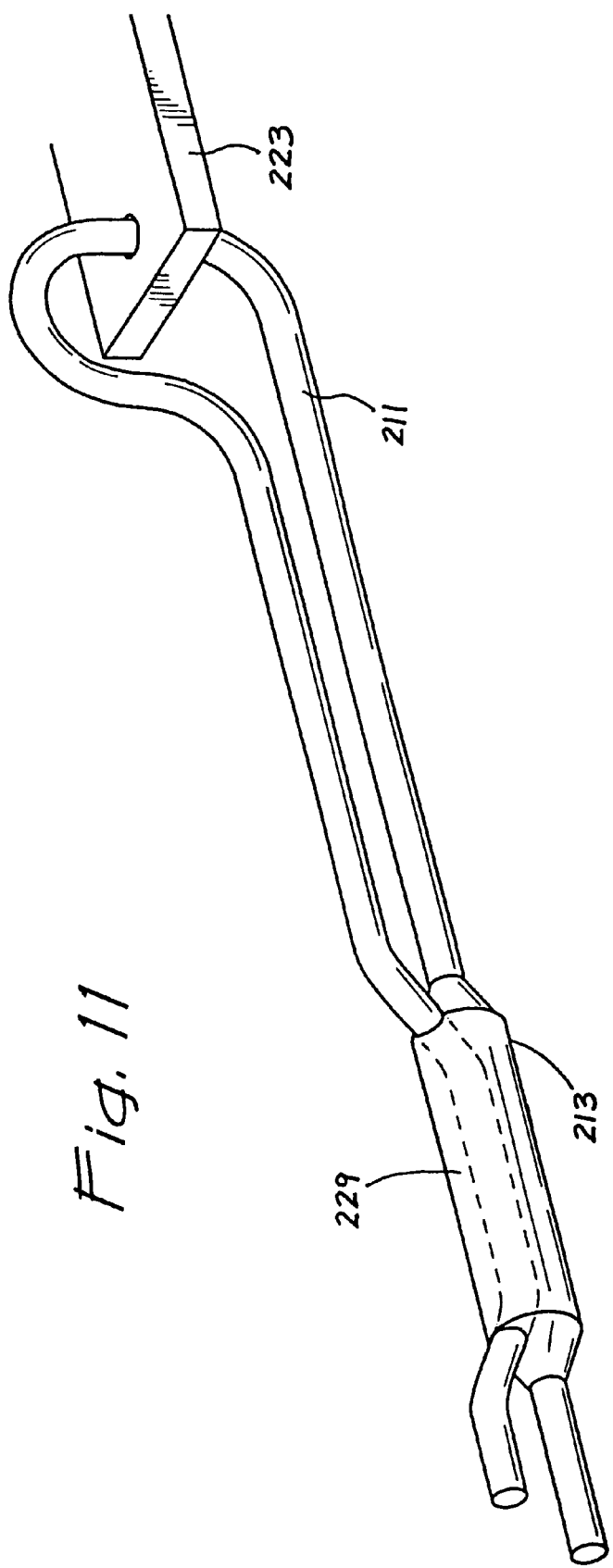
Figure 12:
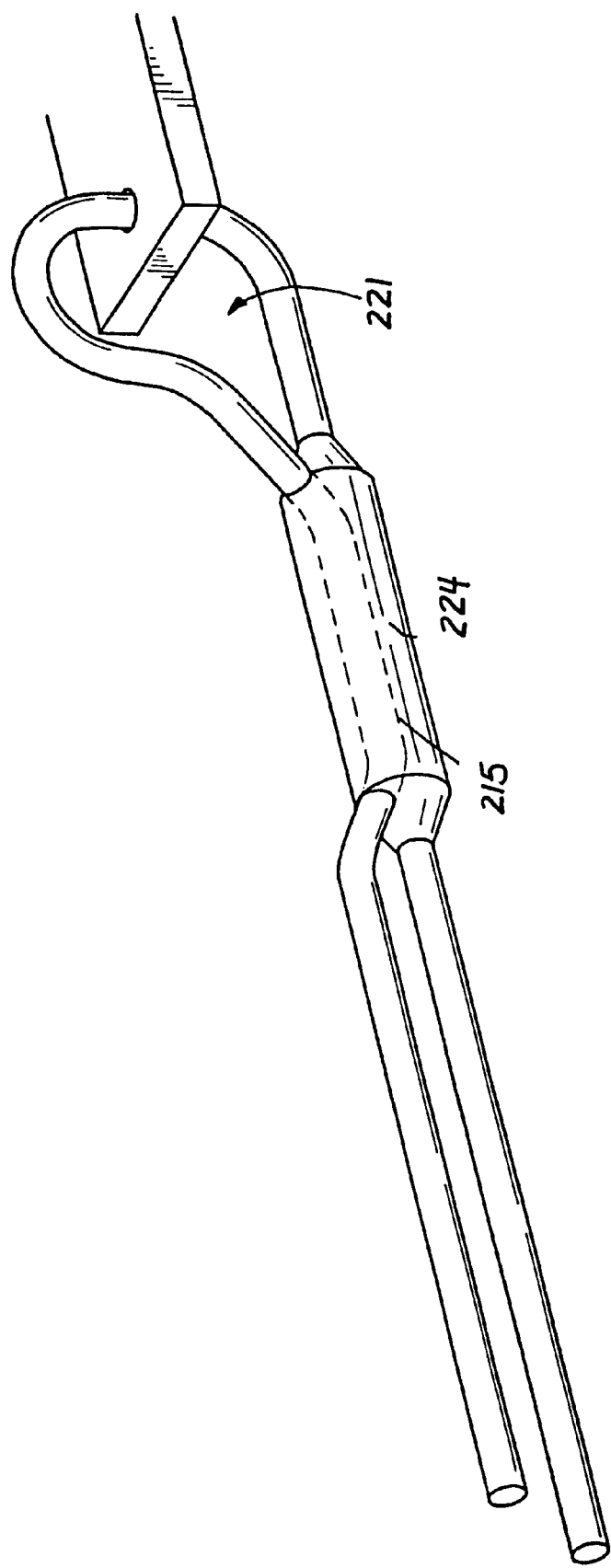
Figure 13:
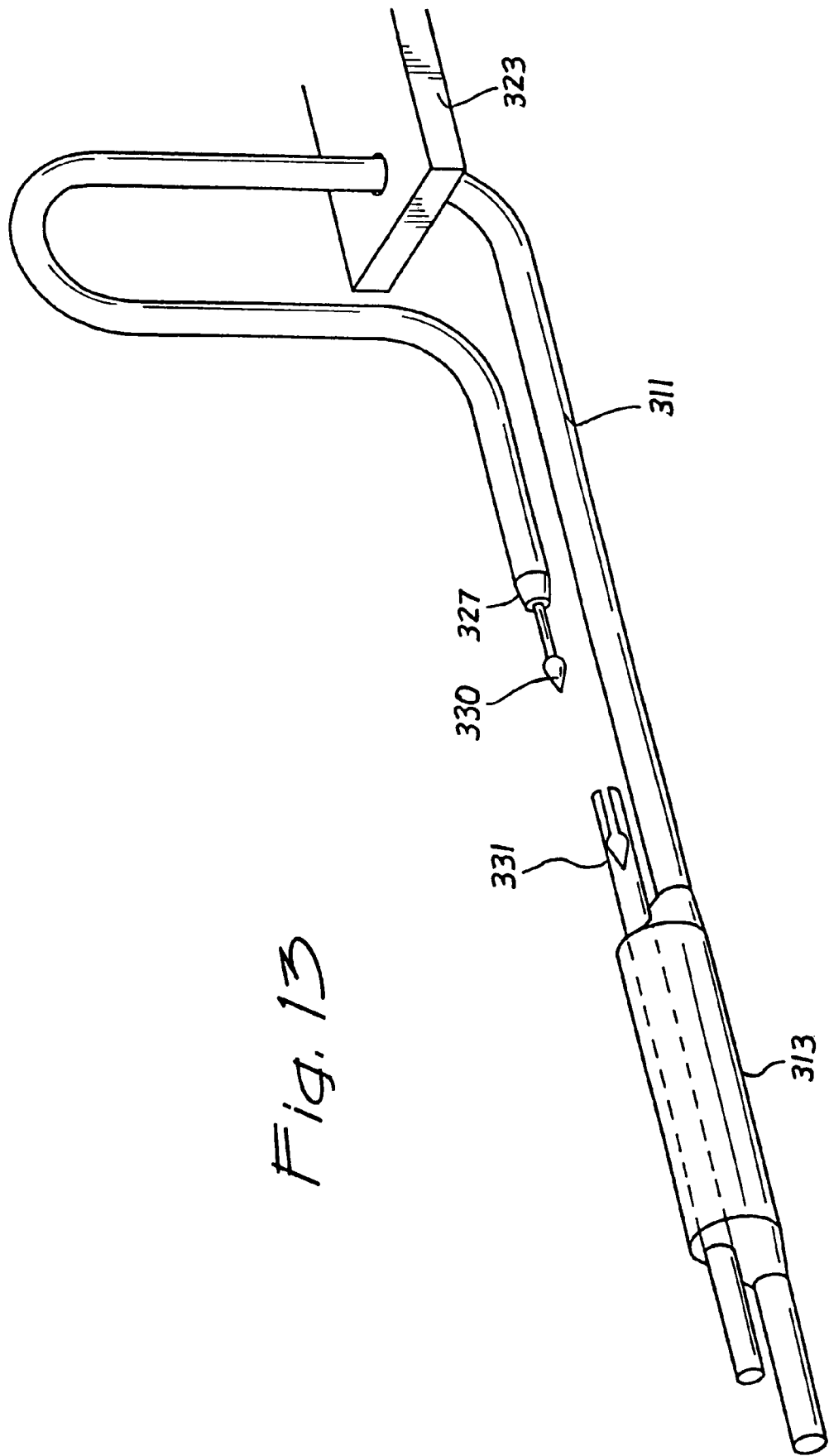

Now with particular reference to FIGS. 8–12, there is illustrated a second preferred embodiment of this bound interface, wherein like or functionally equivalent elements to those in previous embodiments are designated by like reference numerals, preceded by the numeral 2. In this embodiment, a suture loop 221 is to be attached to a piece of tissue 223. Suture loop 221 is comprised of a suturing material 211 which is of a braided construction. This braided construction allows a fid in the form of a hook 227, which includes a distal hook portion 30, to pass through the center of a compressed portion 213 of the braided suture 211. The hook 227 is passed through the tissue 223 by common instruments of the art. A flexible loop 31 resides in the interior of the compressed portion 213 and functions to aid in the management of the hook 227 as it travels through the compressed portion 213. The hook 227, and, in particular, the distal hook portion 30 thereof, is placed in the distal portion of the flexible loop 31, as shown in FIG. 9. The hook 227 is then drawn into the interior of the compressed portion 213 of the suture and through a port 35 into the interior lumen 229 within the compressed portion 213 by pulling the proximal end of the flexible loop 31, as shown in FIG. 10. The hook 227 is then drawn out of the compressed portion 213 of the suture and optionally clipped off (FIG. 11). The compressed portion 213 of the suture is then pushed, sliding it along the suture 211 to create the desired loop geometry 221, as illustrated in FIG. 12. Tension is then applied on the compressed portion 213 of the suture to generate a bound portion 224 (FIG. 12) of the suture having a binding interface 215, the binding interface 215 being designed in length and pitch of braid to provide a bound end 224 to the suture loop 221 when suture 211 is in tension.

The flexible nature of the looped component 31 of FIGS. 8–12 is desirable in circumstances that require both ends of the suture to flex in order to manage the suture attachment to the tissue.

FIGS. 13–16 depict another embodiment in which one tail of the suture can be rigid throughout the procedure. In this embodiment, wherein like or functionally equivalent elements to those in previous embodiments are designated by like reference numerals preceded by the numeral 3, a suture 311 is of a braided construction which will allow a fid in the form of a barb 327 to pass through the center of a compressed portion 313 of the braided suture 31. The barb 327 is passed through tissue 323 by common instruments of the art. A rigid component 331 resides in the interior of the compressed portion 313 and functions to aid in the management of the barb 327 as it travels through the compressed portion 313. The barb 327, and, in particular, a distal barb portion 330 thereof, is placed in the distal portion of the rigid component 331, as shown in FIG. 14. The barb 327 is then drawn into an interior lumen 329 of the compressed portion 313 of the suture 311 through a port 335 by pulling the proximal end of the rigid component 331, illustrated in FIG. 15. The barb 327 is then drawn out of the compressed suture 313 and optionally clipped off, as illustrated in FIG. 16. The compressed suture 313 is then pushed to create the desired loop geometry. Tension is applied on the compressed portion 313 of the suture 311 to generate a bound portion 324 thereof, a binding interface 315 being designed in length and pitch of braid to provide a bound end to a suture loop 321 when the bound portion 324 is in tension.

Presented thus far are 3 different manifestations of the self binding suture loop. The first, shown in FIGS. 2–7, addresses an embodiment which lends itself to suturing in an environment where generous flexible access to both suture ends is available. The second embodiment, illustrated in FIGS. 8–12, lends itself to an environment where restricted flexible access to both suture ends is available. The third embodiment, shown in FIGS. 13–16, lends itself to an environment where restricted access is available to both ends of the suture, but one end of the suture can remain rigid throughout the procedure. In all of these disclosed embodiments there resides the common requirement of one suture end 27, 227, 327, for negotiating a path through the compressed suture 13, 113, 213, 313. In two of the embodiments, receptacles 31, 331 are utilized to receive the suture end 27, 327, respectively.

The fid 27 in FIGS. 2–7 represents a preferred embodiment of a fid, in the form of a needle, which will pass easily through the internal lumen of the braided suture 113. A specific procedure may require the fid 27 to be sharp or pointed for the purposes of easily navigating through tissue, as shown in a fid 27a in FIGS. 17b and 17c. Should this be the case, it is preferred that a cap 37 be employed (FIGS. 17a and 17c), which fits snugly and securely onto the tip of the fid 27a, for the purposes of easily navigating through an interior lumen 29 (FIG. 3).

Figure 18:
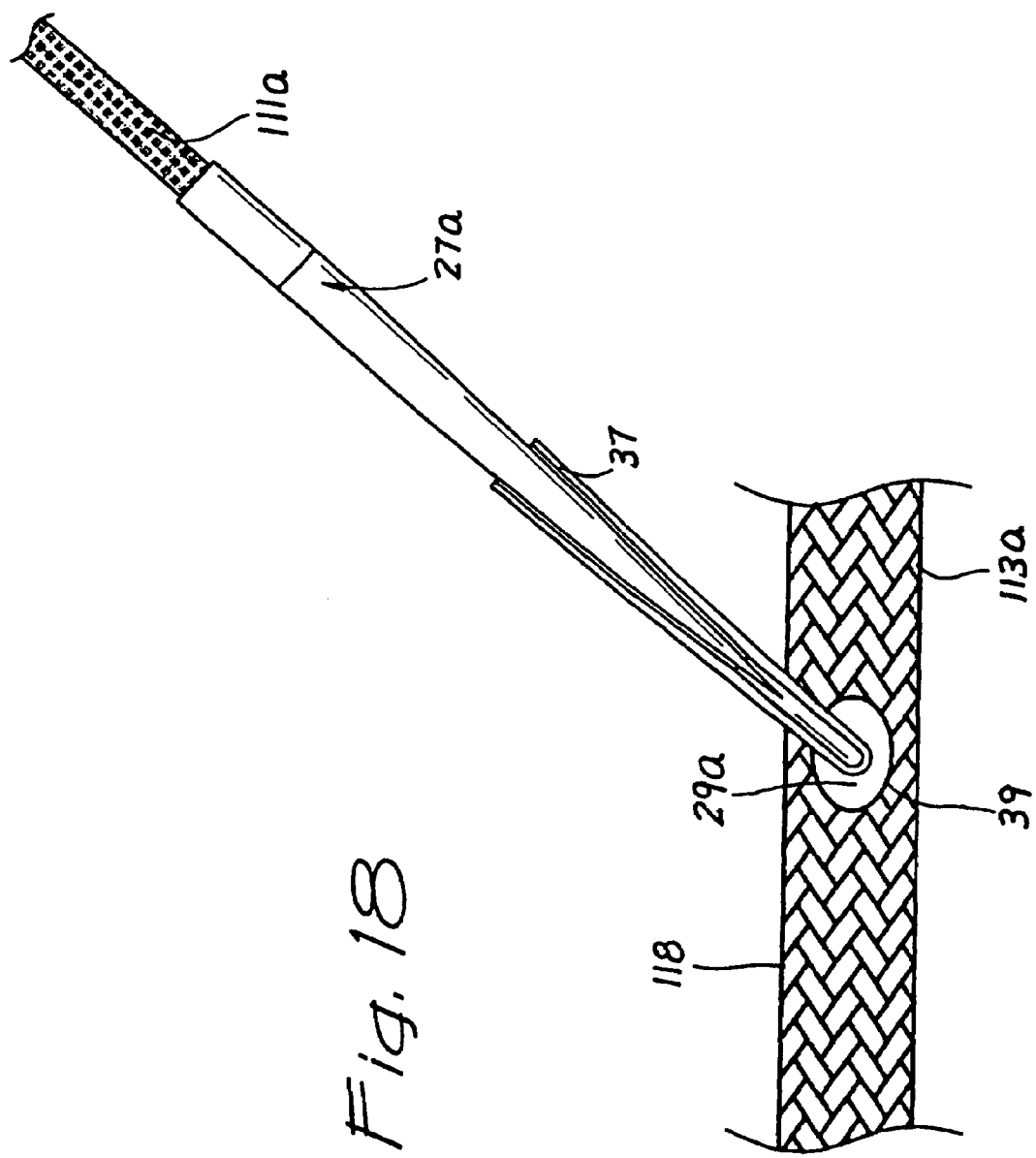

If it becomes difficult to access the interior lumen 29a of the compressed braid portion 113a with any of the devices shown in the previous embodiment, FIG. 18 illustrates a modified embodiment of the invention which includes a grommet 50, either flexible or rigid, that functions to supplement access of the fid 27a of FIG. 17c, for example, into the lumen 29a of the compressed suture portion 113a. The example shown is illustrative only, in that such a grommet could be incorporated into any of the prior embodiments heretofore illustrated.

Figure 19:
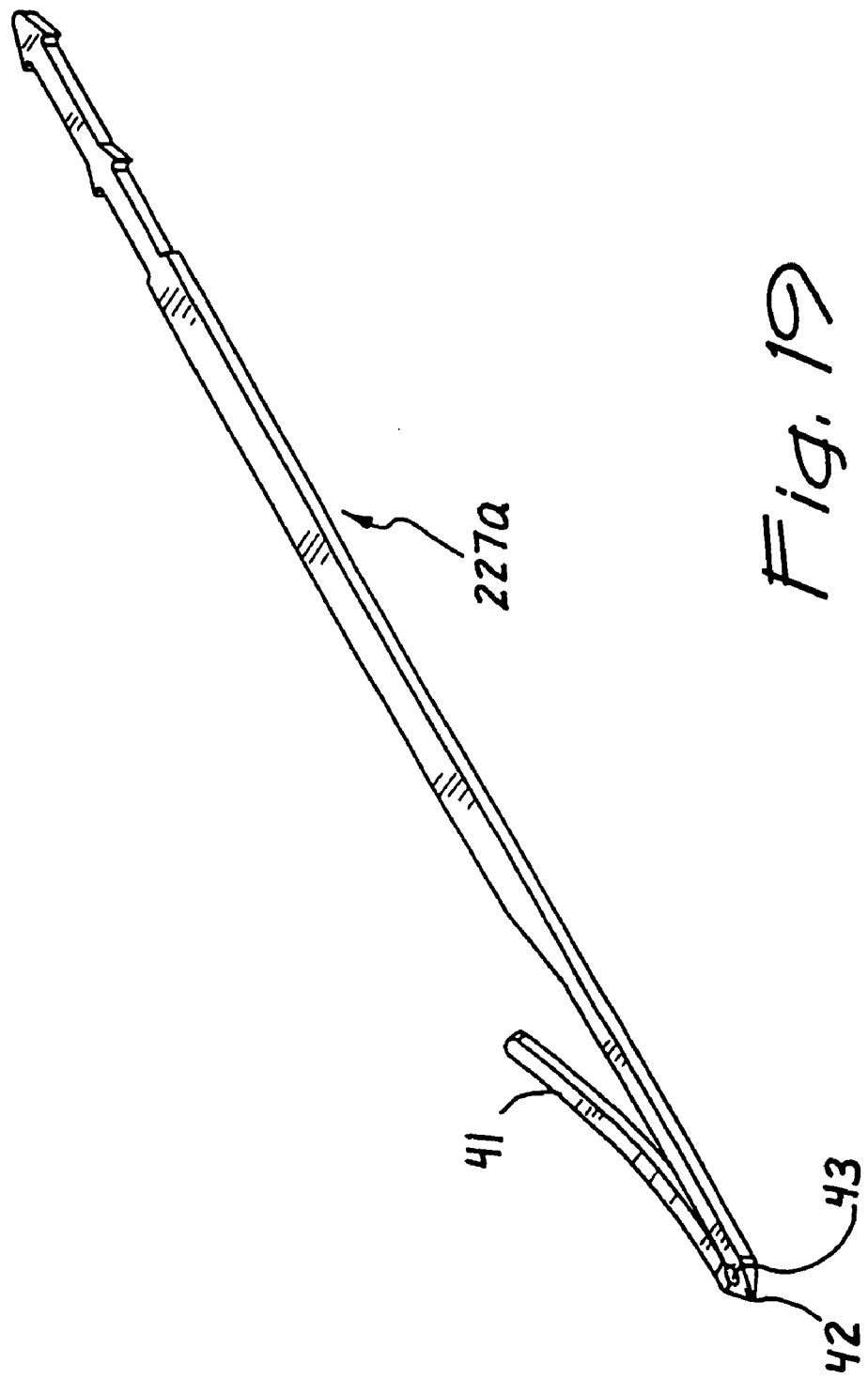
FIG. 19 is a detail perspective view of another embodiment of a fid.

FIG. 19 illustrates an alternative embodiment to that illustrated in FIG. 8, for example, wherein hook 227 is utilized to engage the flexible loop 31. Such hooks 227 are not preferred in all sizes of sutures or in all procedures. In smaller environments, where visualization of the hook can be difficult, it is preferred to utilize a hook 227a, as shown in FIG. 19, which has a tab portion 41 that is predisposed to accept a suture loop. As shown, the hook 227a also includes a piercing tip 42. The tab portion 41 protrudes outwardly in a manner that makes it easy to capture a suture loop, such as suture loop 31 shown in FIG. 8. After the suture loop is captured, the tab portion 41 is sufficiently flexible so as to permit the suture loop to slide distally into an eyelet 43. Once connected to the eyelet 43, the suture loop draws the tab portion 41 into the interior of the braided suture.

Figure 20:
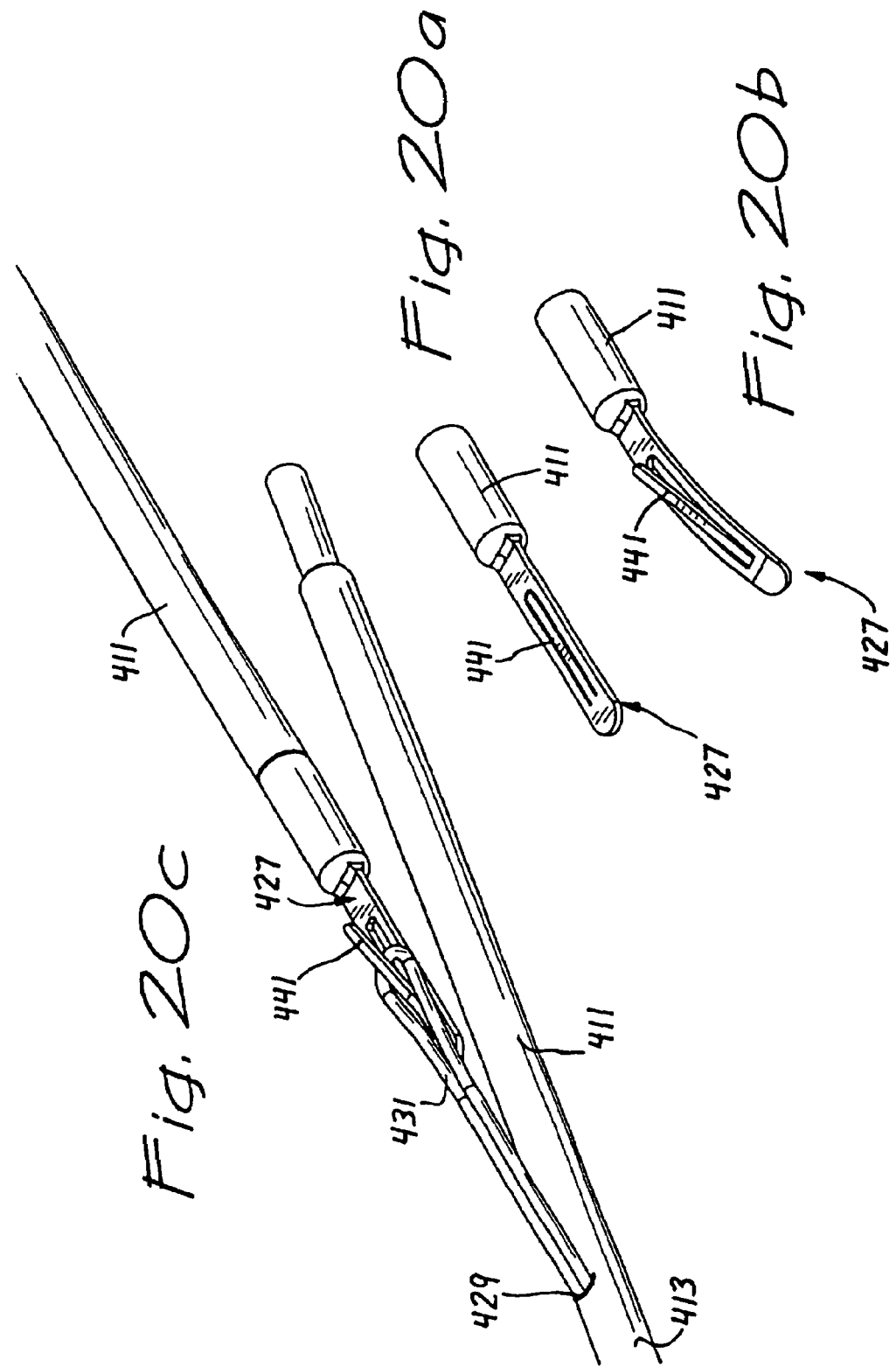
FIGS. 20a through 20c are detail perspective views of an additional fid embodiment.

FIGS. 20a–c, wherein like or functionally equivalent elements to those in previous embodiments are designated by like reference numerals preceded by the numeral 4, show an additional alternative embodiment for a hook-type fid device which is preferred in larger suture sizes in normal visualization environments. Referring now to FIG. 20a there may be seen a suture 411 to which is attached a hook 427, which includes a tab portion 441. The tab portion 441 is made accessible by bending the hook 427 as shown in FIG. 20b. FIG. 20c illustrates a loop portion 431 that has been looped around the tab portion 441. This mechanical attachment will allow for the suture 411 to be pulled into an interior lumen 429 within a compressed portion 413 of the suture 411.

Figure 21:
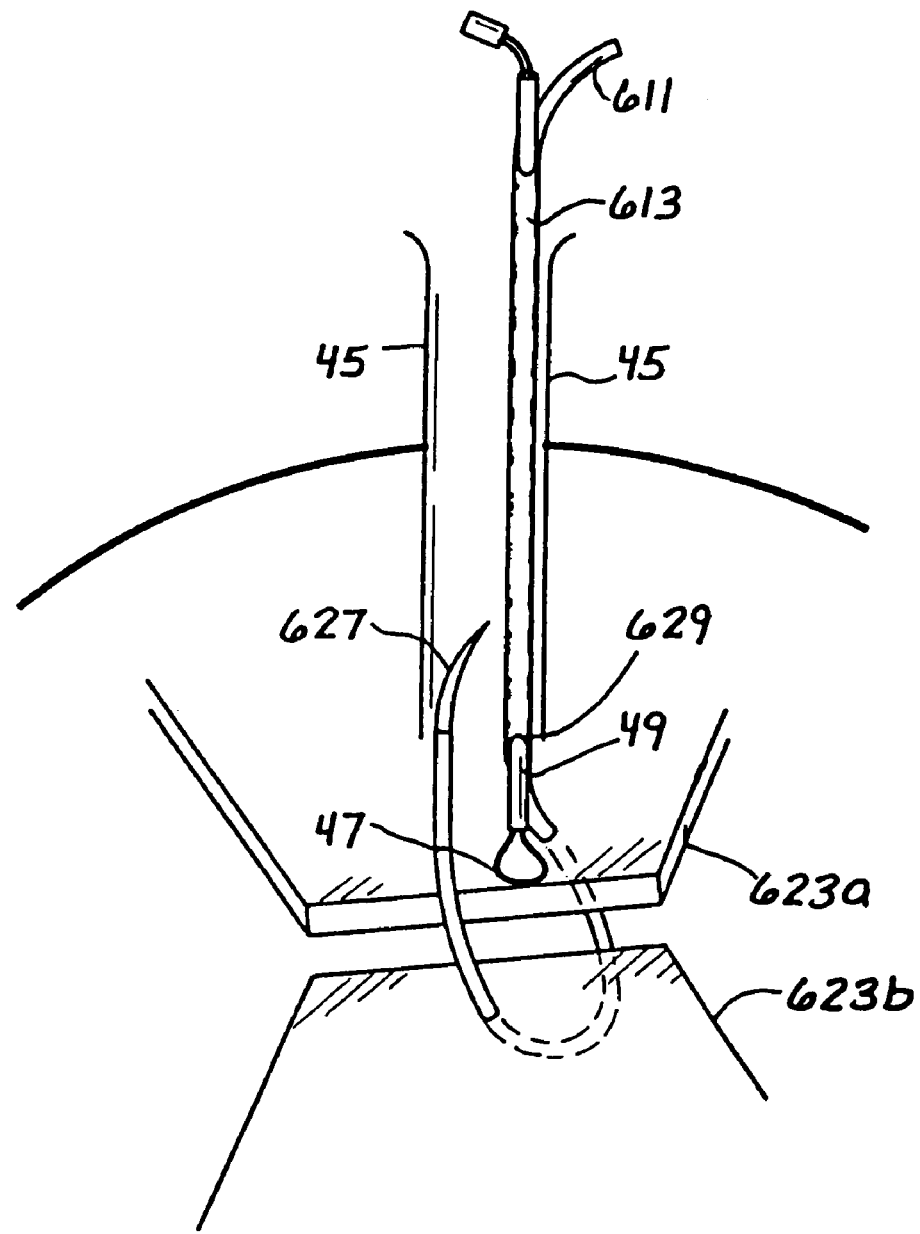
FIGS. 21 through 27 are schematic perspective views illustrating in sequence yet another alternate apparatus and method for forming a single tail suture in accordance with the present invention.
Figure 22:
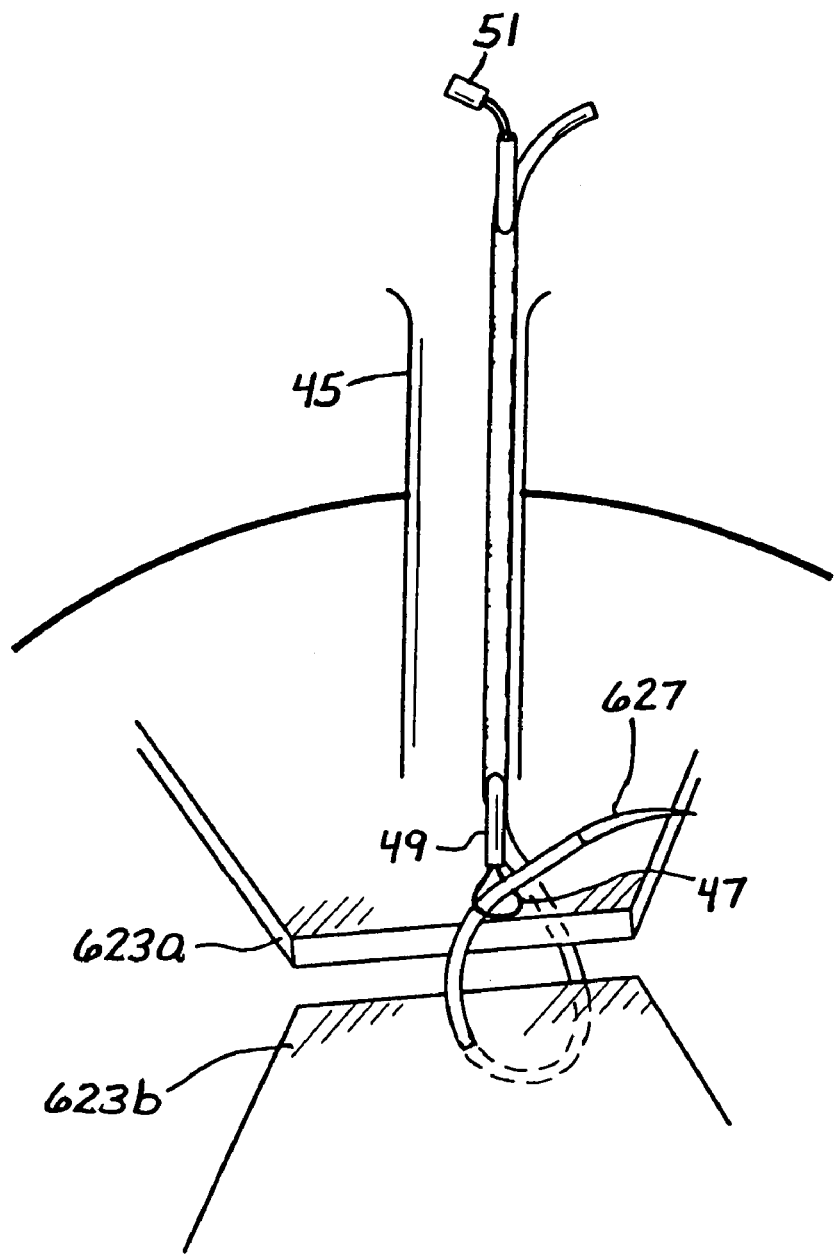
Figure 23:
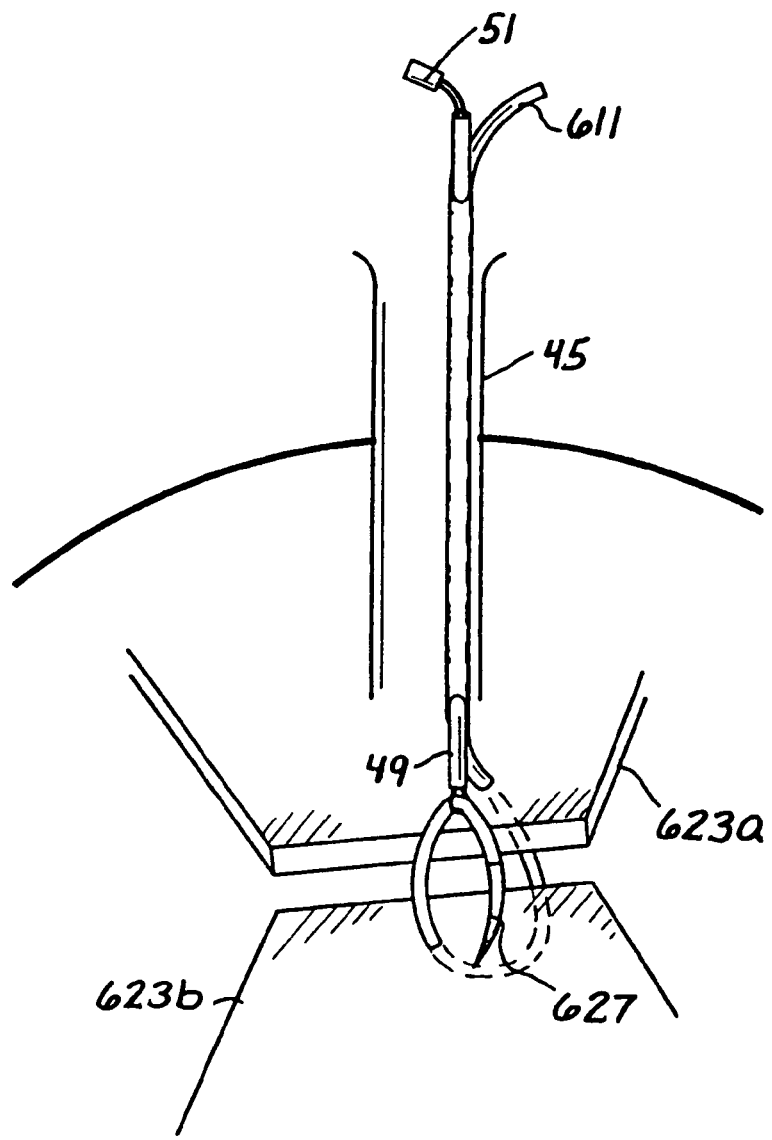
Figure 24:
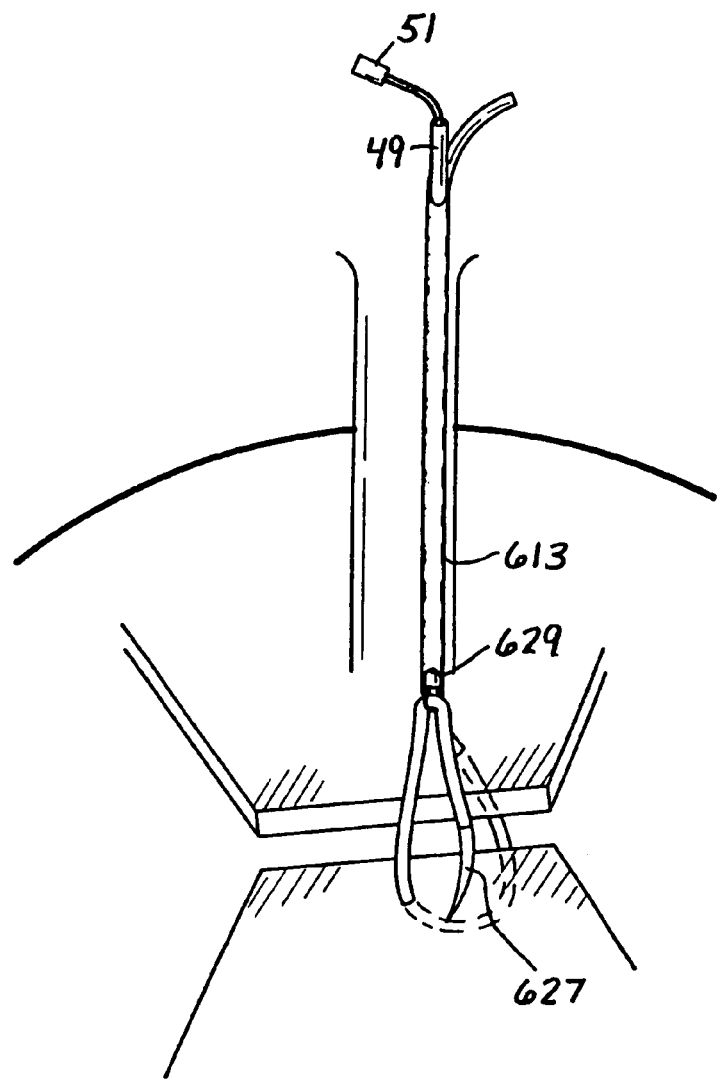
Figure 25:
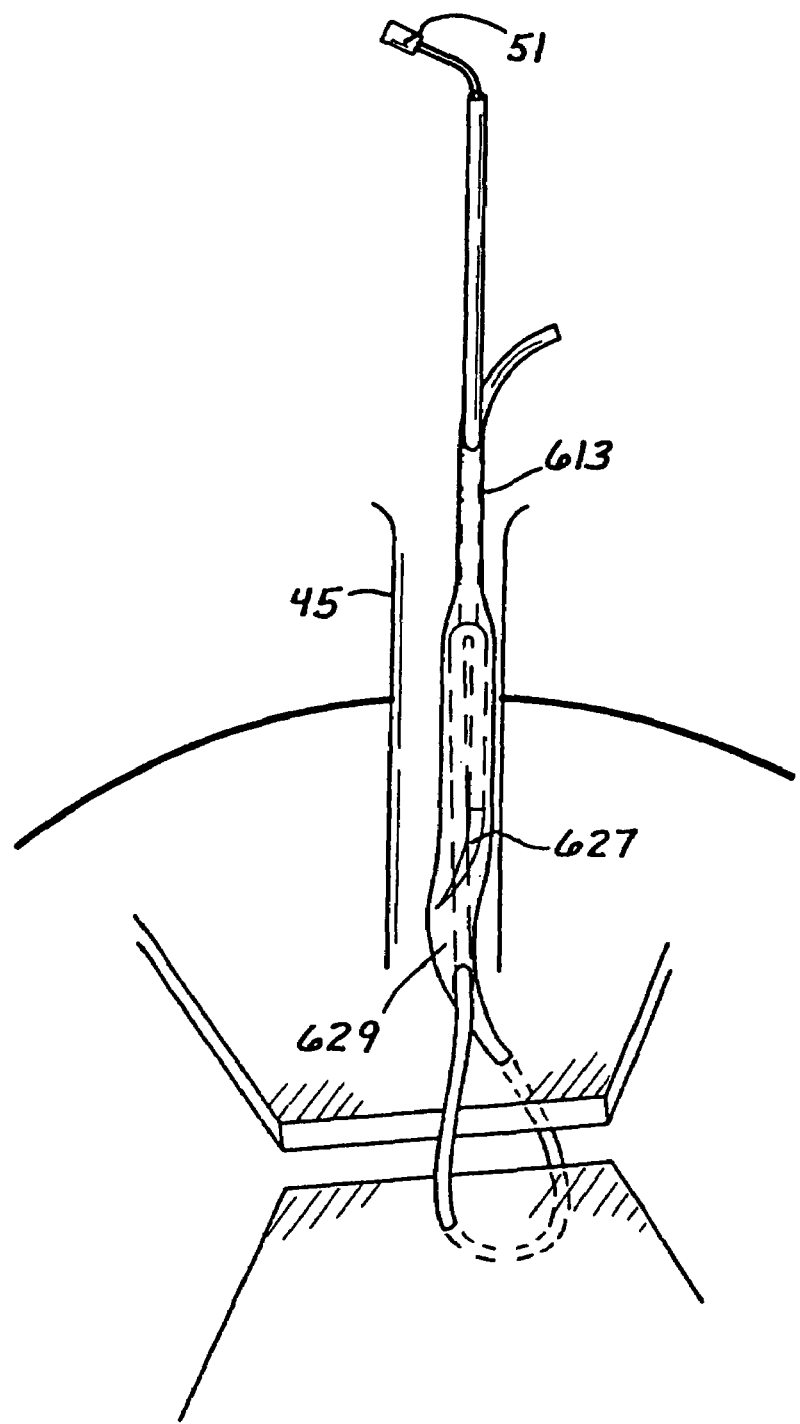
Figure 26:
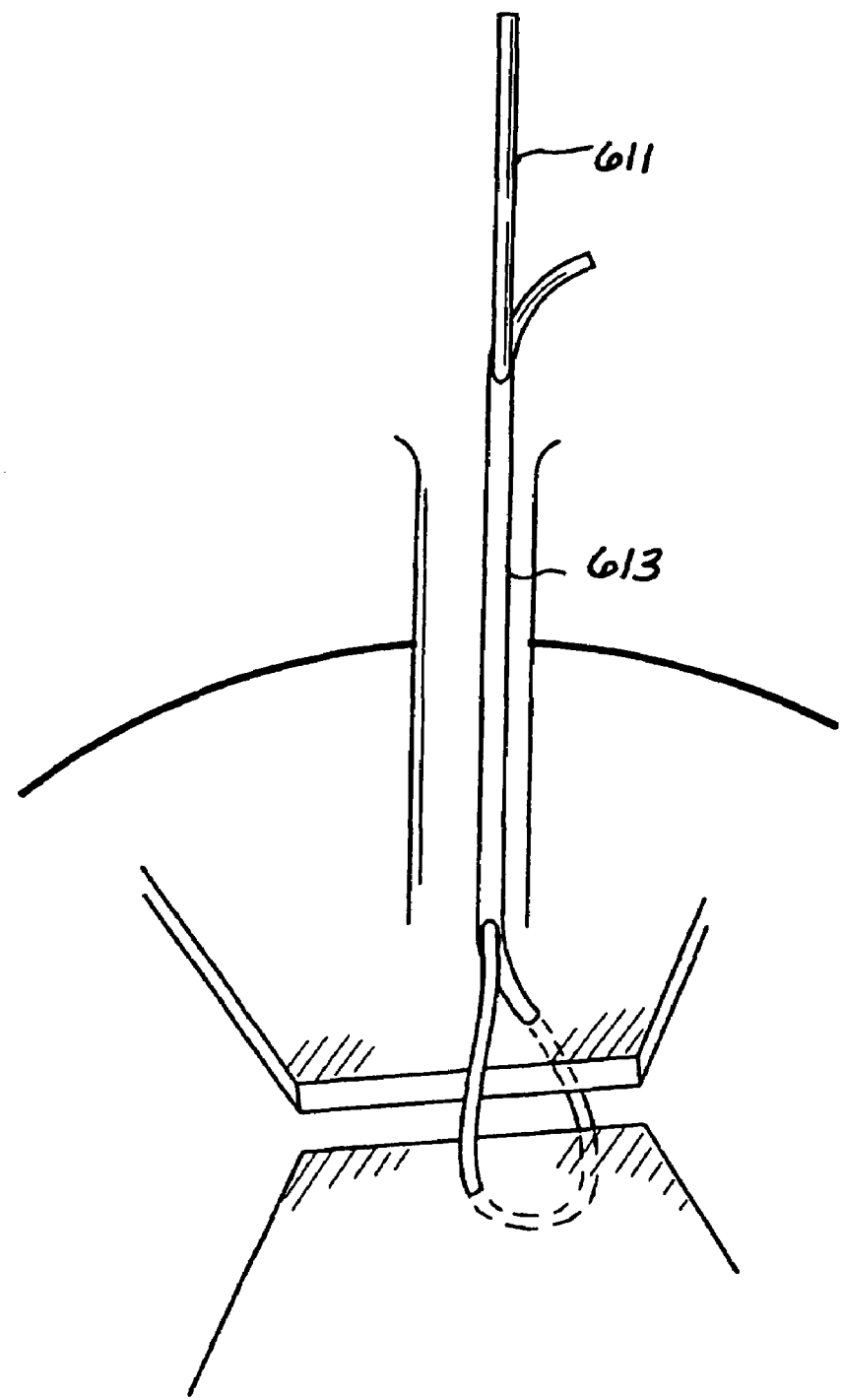
Figure 27:
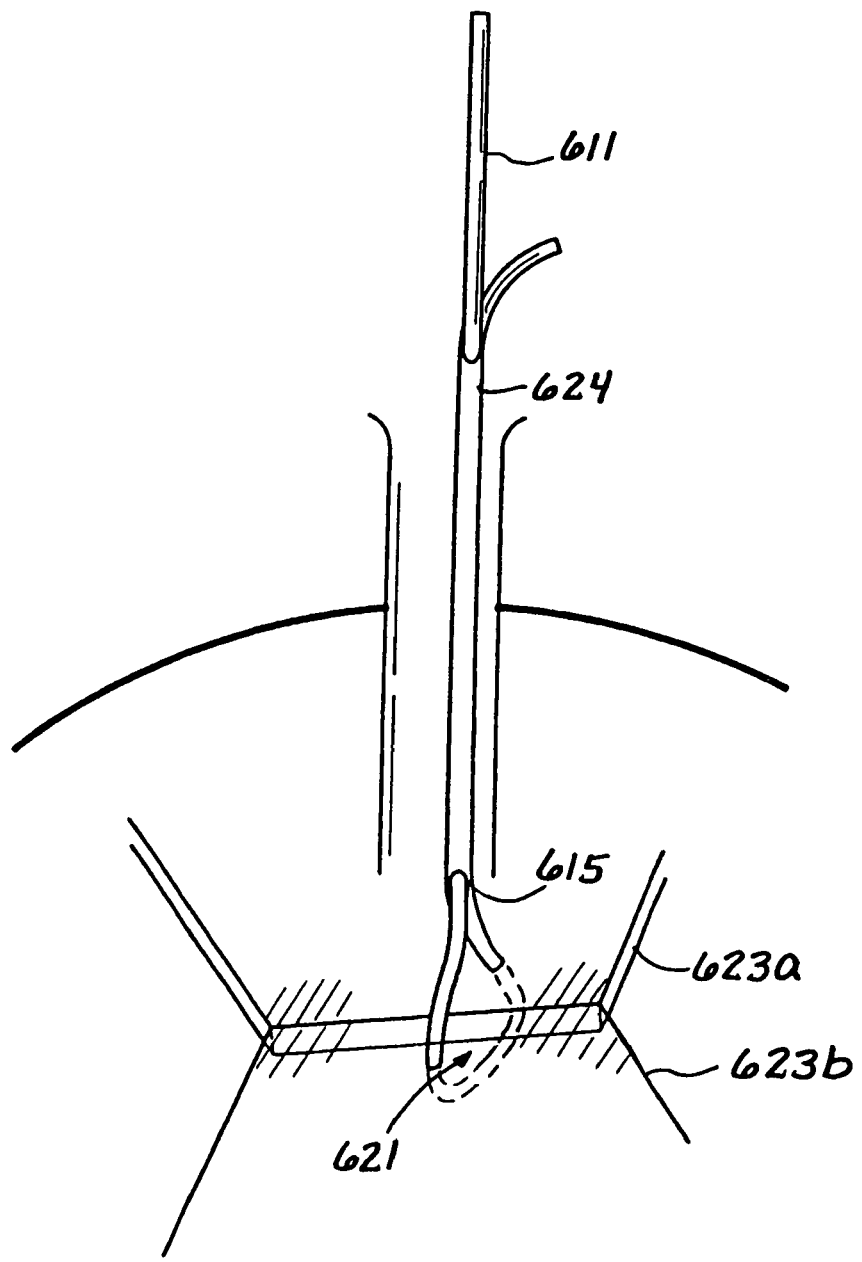

FIGS. 21–27 illustrate a method by which a self binding suture is used to attach two pieces of tissue together. In this embodiment, like or functionally equivalent elements to those in previous embodiments are designated by like reference numerals preceded by the numeral 6. Two pieces of tissue 623a,b are beneath the skin and accessed via a cannula 45. A fid in the form of a needle 627 attached to the end of a suture 611 is passed through both pieces of tissue 623a and 623b using conventional methods, as shown in FIG. 21. The fid 627 is then passed through a loop 47 at the distal end of a snare 49, as shown in FIG. 22. The snare is pulled tight by pulling on a tab 51 at a proximal end of the snare 49, as illustrated in FIG. 23. The snare 49 is then pulled up into the interior lumen 629 of the compressed braided suture 613, dragging the fid 627 along with it (FIGS. 24 and 25). The snare 49 is then removed from the suture and the fid 627 is optionally cut off, as shown in FIG. 26. At this juncture, the outer portion of the compressed portion 613 may be pushed down into the cannula 45 while the cut tail of the suture 611 is pulled, creating the forces necessary to draw the tissue portions 623a and 623b together, as shown in FIG. 27. Once drawn together, tension on the binding interface 615 of the suture 611 creates a binding force that locks the proximal ends of the suture together, creating a bound portion 624 of the suture.

Figure 28:
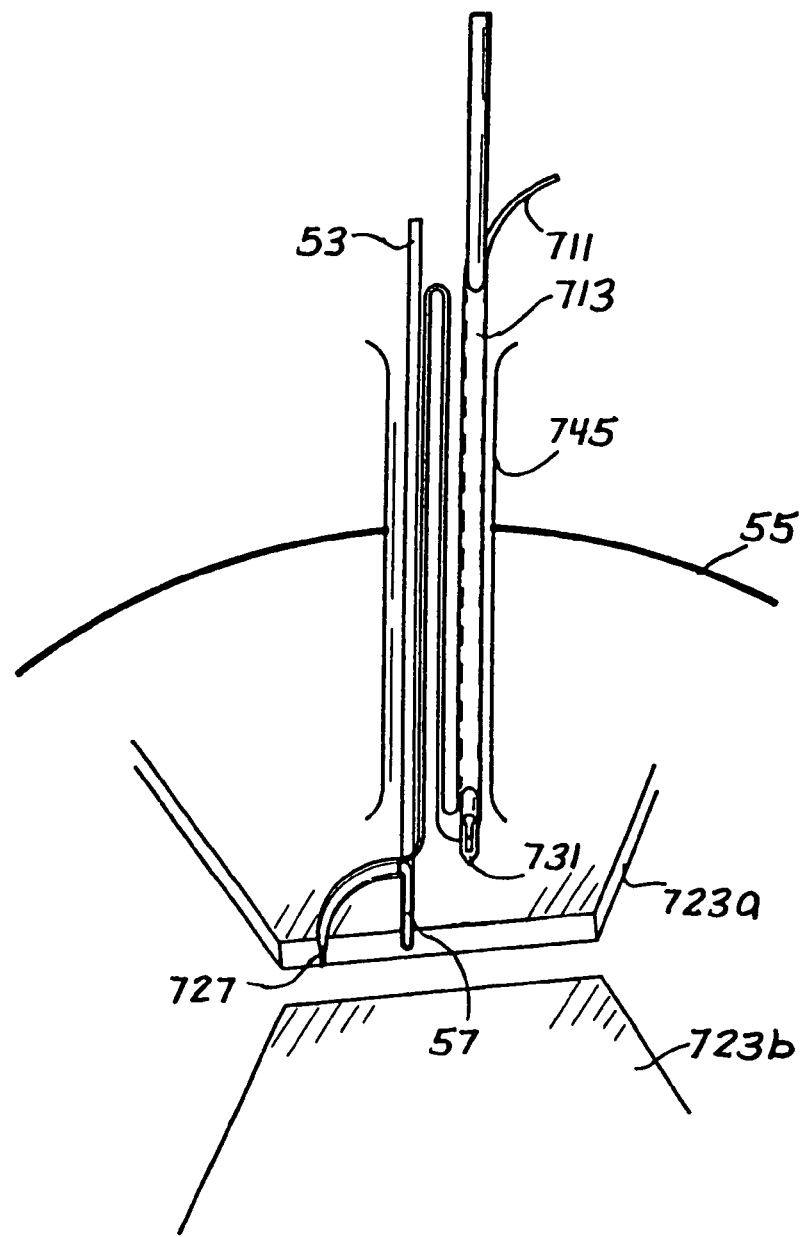
FIGS. 28 through 35 are schematic perspective views illustrating in sequence still another alternate apparatus and method for forming a single tail suture in accordance with the present invention.
Figure 29:
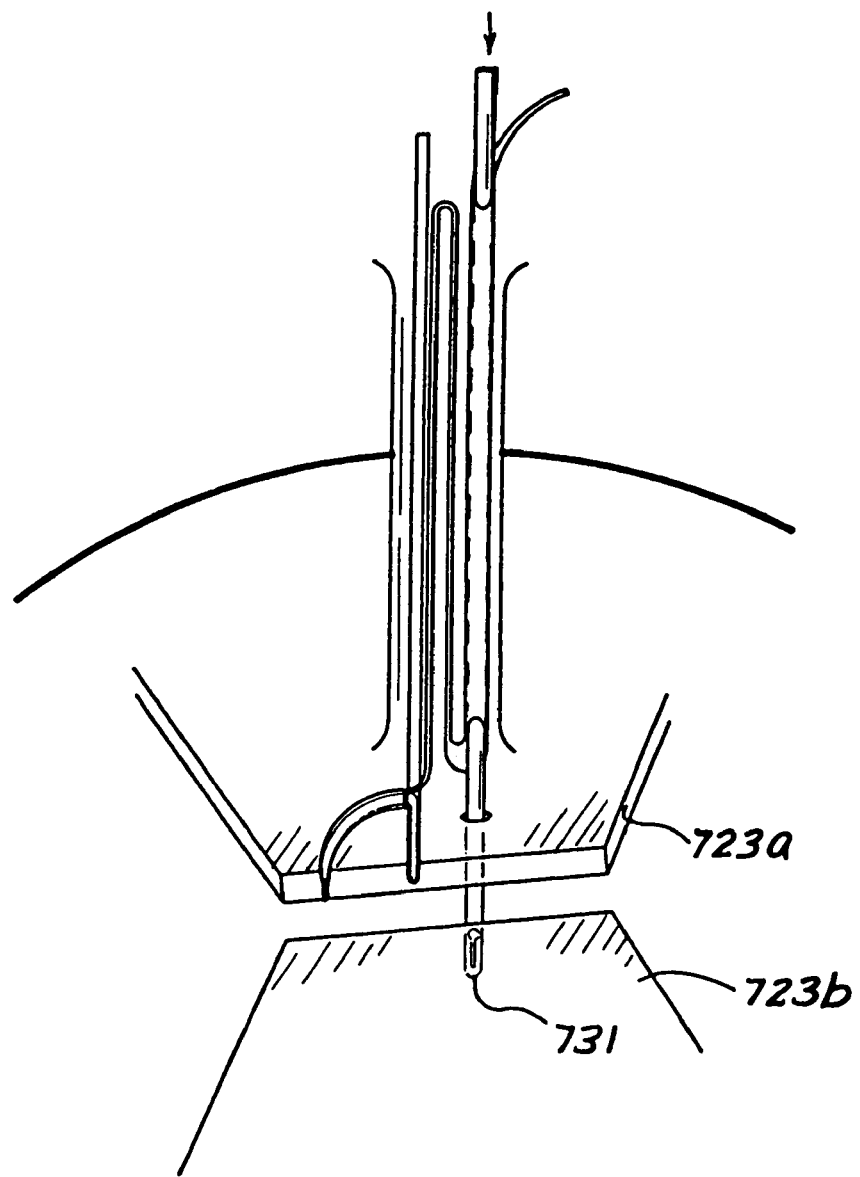
Figure 30:
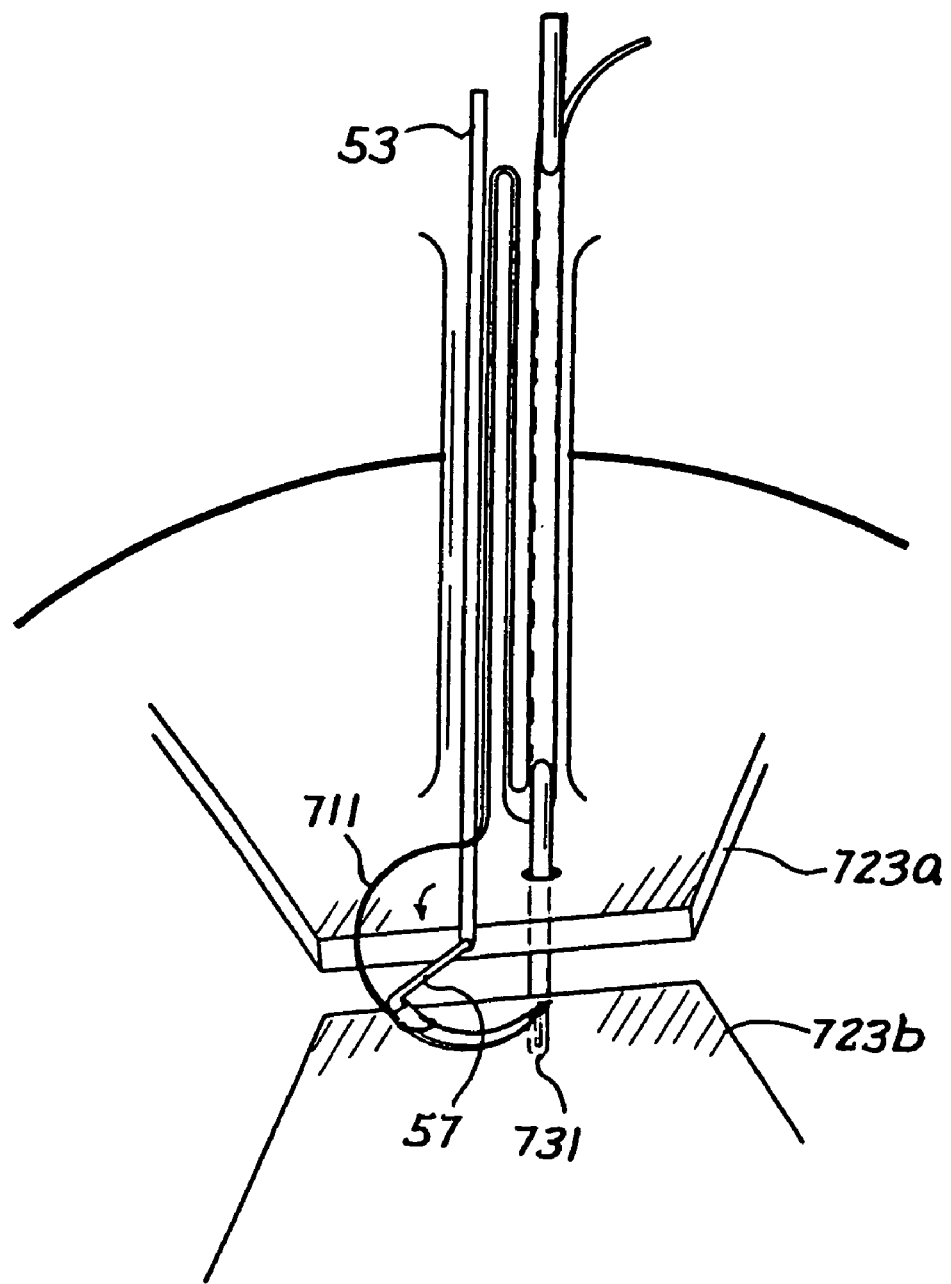
Figure 31:
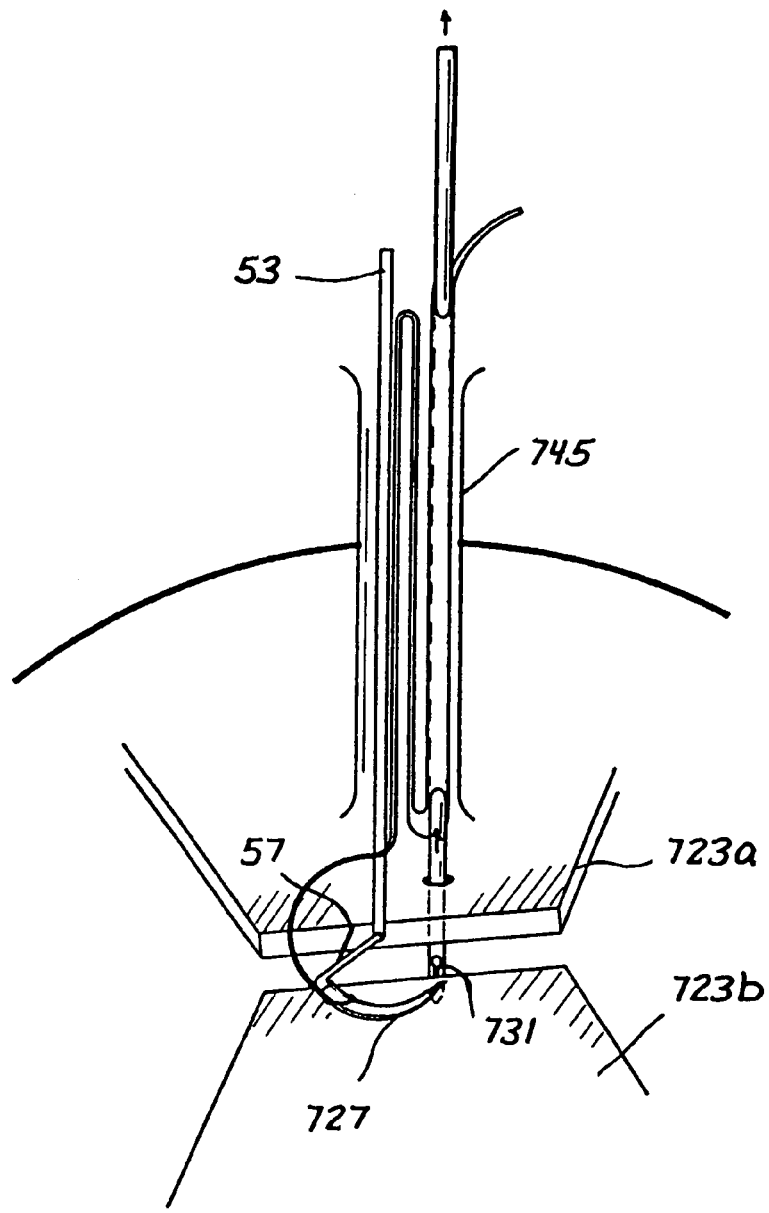

FIGS. 28–35 show another alternative embodiment and method in which the self binding suture concept of the present invention is used in a suturing device to attach two pieces of tissue together. In this embodiment, like or functionally equivalent elements to those in previous embodiments are designated by like reference numerals preceded by the numeral 7. The suturing device in this embodiment comprises a rigid catch 731 that also acts as a piercing element. With reference to FIG. 28, Catch 731 is mechanically linked to a curved needle 727 through an articulating mechanism 53 which is capable of guiding the needle 727 into the distal features of the catch 731. Two pieces of tissue 723a, 723b are beneath a patient's skin 55 and accessed via a cannula 745. The catch 731 is pushed into the tissue 723a, 723b so that its distal end pierces the tissue, as shown in FIG. 29. The articulating mechanism 53 is then actuated so that a piercing driver 57 drives needle 727 through the opposing tissue 723a, 723b and into the catch 731, as illustrated in FIG. 30. Catch 731 is then pulled up to catch needle tip 727, as shown in FIG. 31.

Figure 32:
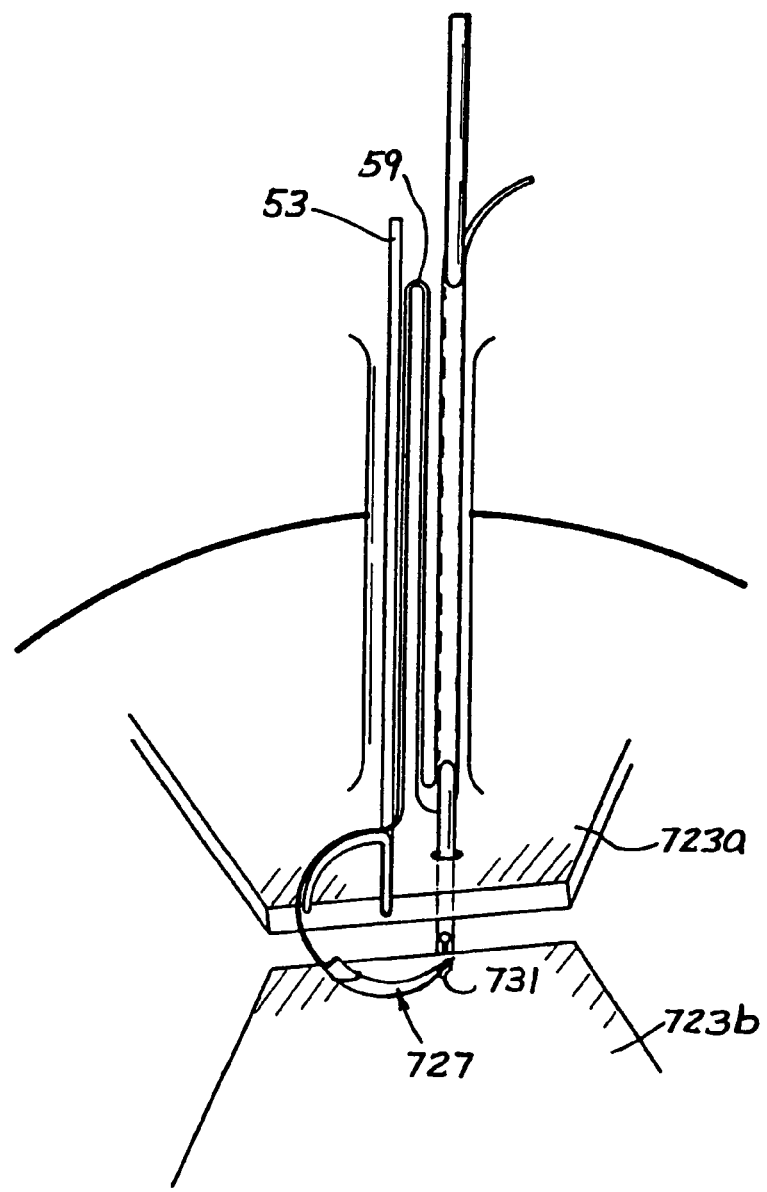
Figure 33:
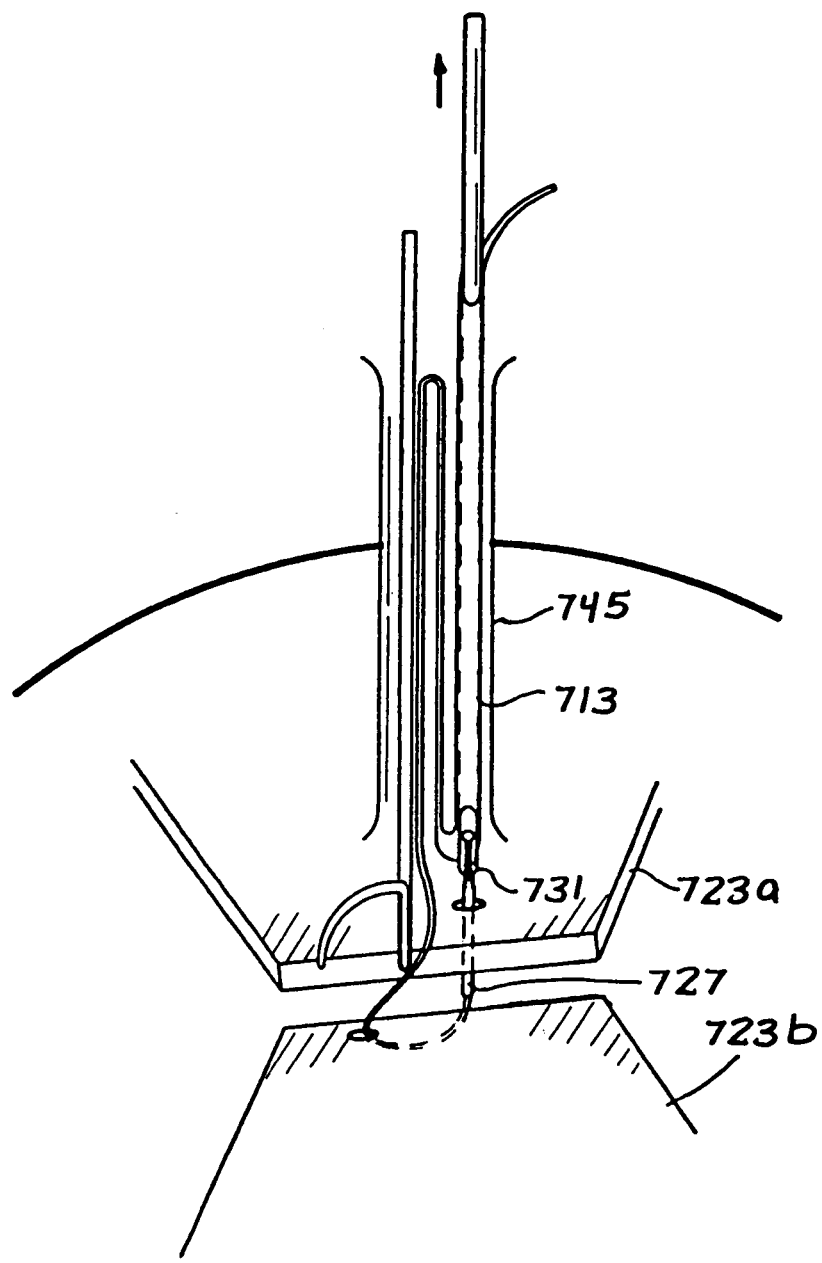
Figure 34:
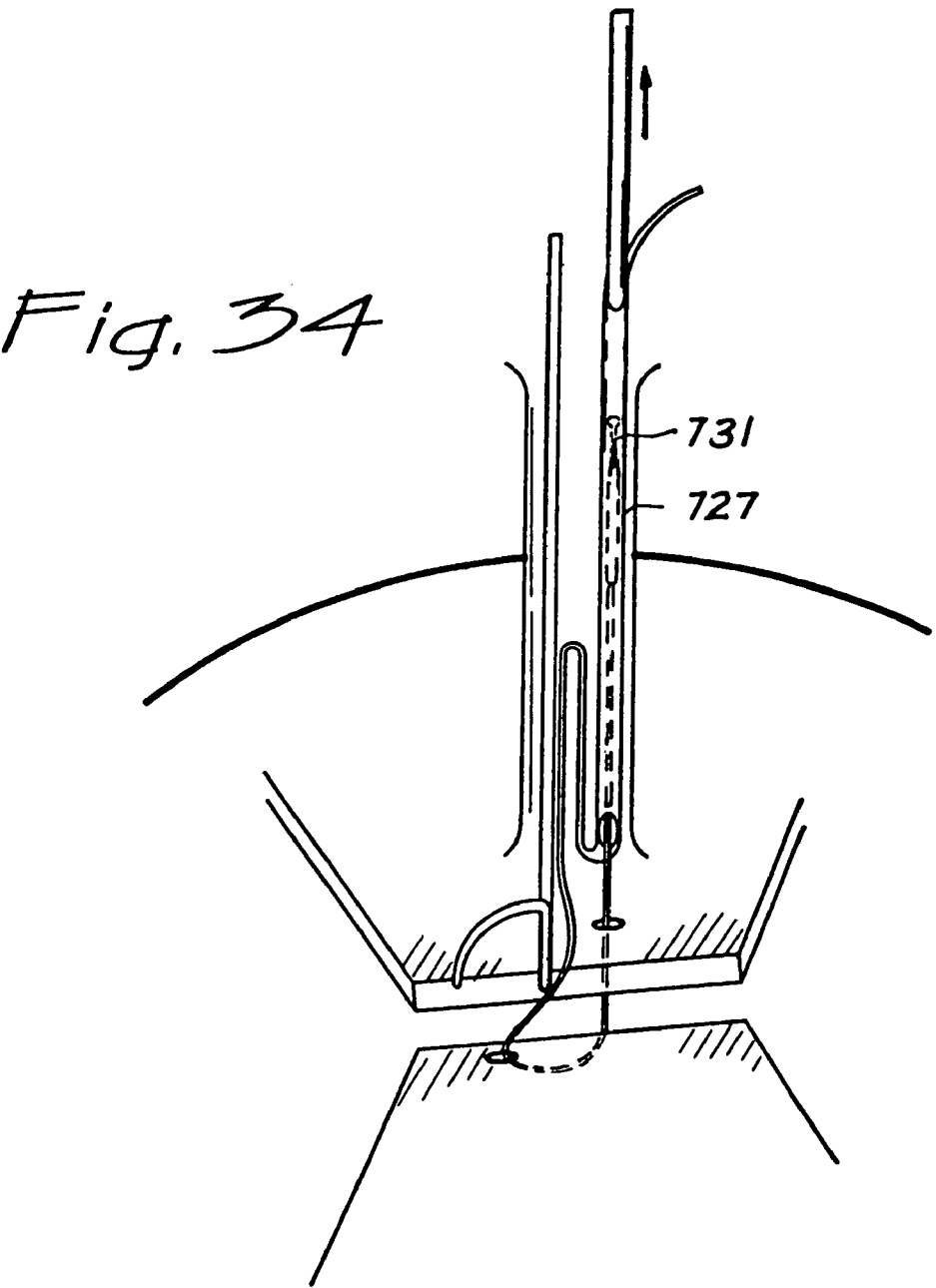
Figure 35:
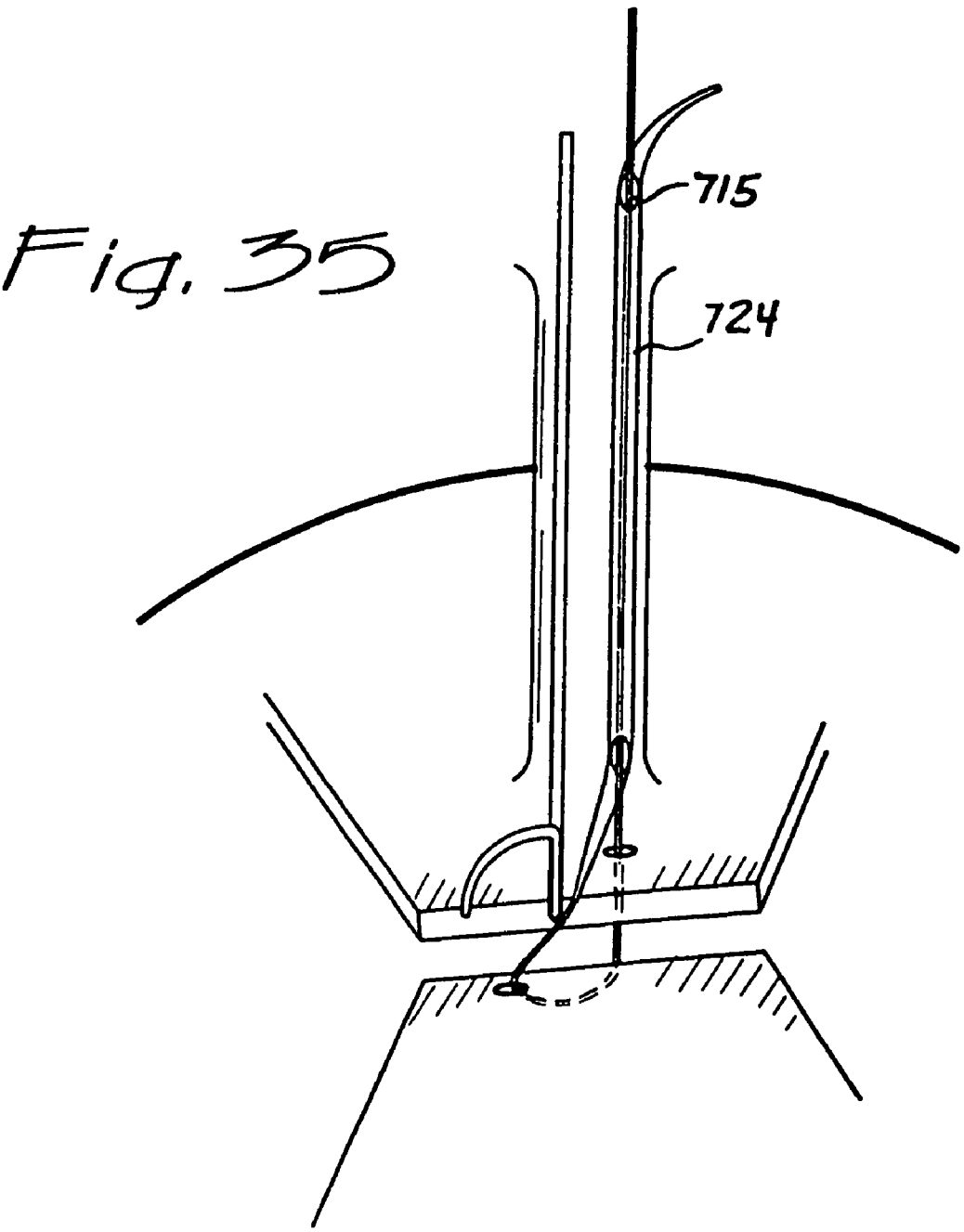

At this point, the articulating mechanism 53 is reversed to back out piercing driver 57 from the needle tip 727 (FIG. 32). The needle tip 727 is rigid, in order to provide for a secure engagement with catch 731. The proximal end 59 of the needle 727, however, is formed of a flexible material so as to enable the needle tip 727 and its supporting portions to follow the catch 731 upwardly into the compressed portion 713 of the suture, as shown in FIGS. 33 and 34. When the catch 731 is withdrawn from the compressed portion 713, as illustrated in FIG. 35, thereby pulling the needle 727 along, a binding interface 715 is formed along a bound portion 724 of the suture.

In the preceding described self-binding suture embodiments, the elements common to each are as follows:
1) a braided tensioned suture represented by reference numerals ending with "11" (hereinafter designated as "11");
2) a portion of the suture 11 that is radially expanded as a result of it being under compression, represented by reference numbers ending with "13", hereinafter designated as "13", through which one tail of the suture 11 is threaded, optionally with the aid of a fid or similar tapered rigid portion, represented by reference numbers ending with "27", herein designated by "27";
3) a catch or loop, represented by references numbers ending with "31", herein designated as "31".

Once the tail 27 is threaded back through the expanded portion 13 of the suture, tension on the expanded portion 13 draws the suture down on the suture tail 27 to create a binding interface represented by numbers ending in "15", herein designated by "15". The tension that is put on the expanded portion 13 must be applied in a specific manner to be most effective. The tension must preferably be applied continuously in a constant motion starting at the distal end of compressed suture portion 13 and moving toward the proximal end thereof. This is most easily accomplished by grasping the distal end of suture portion 13 between the thumb and fore finger and sweeping the length of thereof to its proximal end while holding the threaded tail 27 in the other hand. Many applications of the invention provide for such manual access to the distal and proximal ends of compressed suture portion 13 and need no other devices for the creation of the binding interface 15. However, there are other potential applications of the inventive concept for which access to the proximal and distal ends of the compressed suture portion 13 are limited.

Figure 36:
FIG. 36 is a perspective view of an inventive tool which may be used for tensioning a single tail suture.

In such applications, FIG. 36 illustrates a device or, more particularly, a tensioner 63 which provides a means for applying the proper amount of tension to the compressed suture portion 13, from its distal end to the proximal end thereof, in order to create the bound suture portion 24, comprising a binding interface 15 between the expanded suture length and the tensioned suturing ma through its internal lumen. The tensioner 63 includes a shaft 65 that is long enough to allow sufficient access to the distal end of the compressed portion 13. At the end of this shaft is disposed a head 67 having a slot 69, wherein the head is formed of material which will frictionally interact with the suture so as to apply the desired frictional tension thereto when portions of the compressed suture 13 extend through the slot. In operation, the tensioner shaft 65 is manipulated so that the head 67 is disposed at the distal end of the compressed suture portion 13, whereupon the suturing material is engaged within the slot 69. Then, the tensioner 63 is withdrawn proximally toward the practitioner, thereby functioning to "smooth down" or tension the compressed suture portion 13 as it travels therealong.

Figure 37:
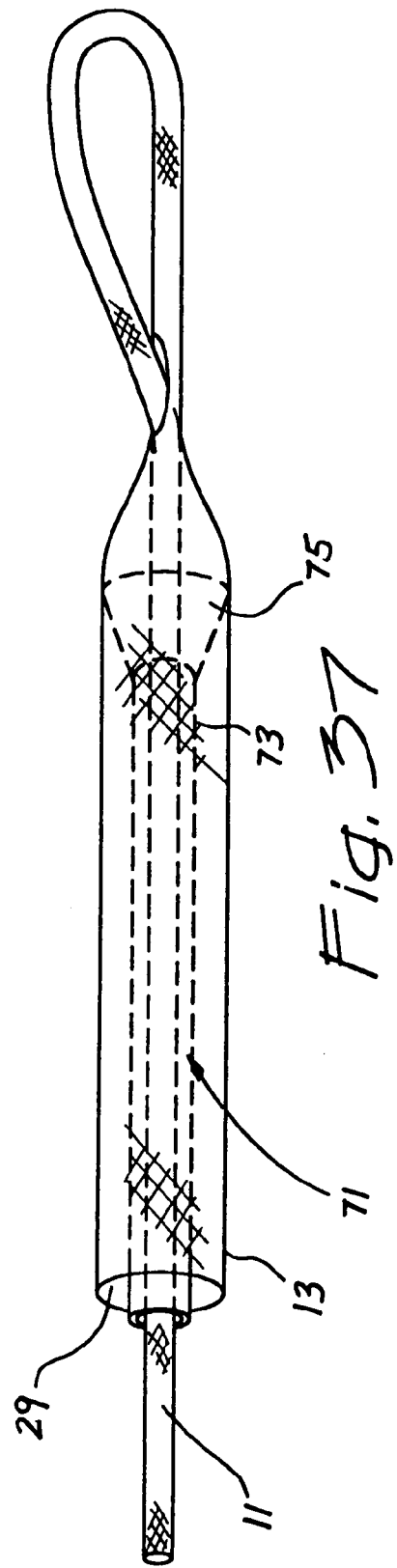
FIG. 37 is a perspective view of an alternative tensioning tool for use in tensioning a single tail suture.

Another provision for a tensioner is one which may be integrated into the suture, in either a rigid or flexible manner, is shown, for example, in FIG. 37. In this embodiment, a modified tensioner device 71 is illustrated, which comprises a tubular structure 73. The tubular structure 73 may be fabricated of either flexible or rigid materials, and includes a flared portion 75 at its distal end. The outer dimensions of the flared portion 75 are sufficiently large so that it binds with the interior surface of the lumen 29 within the compressed suture portion 13. This binding interface between the tensioner 71 and the compressed suture portion 13 supplies the tension required to create a binding interface between the compressed suture portion 13 and the suture 11 extending through the lumen 29 thereof when the tensioner 71 is pulled proximally out of the lumen 29. The interior of the tubular structure 73 provides for the passage of all necessary fids, such as hooks, snares, and needles, for assisting passage of the suture 11 through the lumen 29. The flared portion 75 may also have an interior that facilitates the management of fid devices into the interior of the braid.

In all the heretofore disclosed embodiments, the radially expanded section 13 of the suture is held open by compressing that section of the suture. In order to draw a fid into the center of the braid, one hand is required to push on the suture and the other to draw or push the fid 27 into the center of the braid. However, the inventors have discovered a method for holding the braid open throughout the process of managing the fid device that also serves to tension the suture portion 13 in the final stages of creating the binding interface 15. Accordingly, FIGS. 38–43 illustrate such a method. More particularly, FIG. 38 illustrates shows an expanded braid 79 encapsulated in a tubular member 81, wherein the tubular member 81 has an interior lumen 83 large enough to accept a fid 85 that is in the process of completing a suture loop. A preferred approach would be to over-extrude the tubular member 81 onto the braided portion 79 to achieve this configuration. In FIG. 39 there is shown the fid 85 passing through the interior of the expanded braid 79 and exiting proximally. FIG. 40 shows the suture tail 87 completely in the expanded portion of the expanded braid 79.

Once the suture 87 is fully in place within the expanded braid 79, the expanded braid can be tensioned over the suture. This tensioning procedure is illustrated in FIGS. 41–43. Tensioning is accomplished by pulling the proximal portion of the tube 81 with such force, in the direction shown by arrows A, as is necessary to delaminate the braid 79 from the tube's interior surface 88. This force is in a direction and of sufficient strength to tension the binding interface distally to the proximal end as is required, resulting in a bound portion 89 (FIG. 43).

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for performing an arthroscopic surgery using a hollow braided suture, said suture having an outer cylindrical wall and a lumen extending therethrough, said suture further comprising a free proximal end portion, a loop, and a standing end portion, said method comprising:

selecting a tissue to move;
  inserting a cannula through a patient's skin;
  attaching the suture to the tissue;
  moving the tissue by pulling on the free proximal end portion, of the suture, said suture extending though said cannula;
  wherein said loop is formed by threading a length of suture through the lumen of said standing end portion, and wherein said step of attaching the suture to the tissue comprises pulling on said free proximal end portion until said tissue is securely locked by said loop.

2. The method of claim 1 wherein said tissue is a ligament.

3. The method of claim 2 wherein said surgery is a rotator cuff surgery.

4. The method of claim 1 comprising forming the loop through a surgically-created opening in said tissue.

5. The method of claim 1 comprising forming said loop through a first tissue and a second tissue, and moving at least one of said first and second tissues towards one another.

6. The method of claim 1 wherein the attaching step is performed after the step of inserting.

7. The method of claim 1 wherein said standing end portion comprises an expanded configuration allowing the diameter of the loop to be adjusted.

8. The method of claim 1 wherein said standing end portion comprises a compressed configuration when said free proximal end is pulled, whereby said suture becomes locked on said tissue.

9. The method of claim 1 comprising cutting a portion of the suture following said step of moving.

* * * * *

UNITED STATES PATENT AND TRADEMARK OFFICE
CERTIFICATE OF CORRECTION

PATENT NO. : 7,285,124 B2  Page 1 of 1
APPLICATION NO. : 10/750287
DATED : October 23, 2007
INVENTOR(S) : Seth A. Foerster It is certified that error appears in the above-identified patent and that said Letters Patent is hereby corrected as shown below:

Column 15, line 8, delete the text "a loop, and".

Column 15, line 9, after the comma in the word portion please insert --and a loop formed by a length of suture being threaded coaxially through the lumen of said standing portion,--.

Column 15, line 10, before the word selecting please insert --providing said suture comprising said loop formed by a length of suture being coaxially threaded through the lumen of said standing portion;¶--.

Column 15, line 12, after the word suture please insert --loop--.

Column 15, line 13, after the word suture please insert --after said step of attaching the suture to the tissue-- and delete ", said suture extending though said cannula".

Column 15, line 16, please delete the text "wherein said loop is formed by threading a length of suture through the lumen of said standing end portion, and".

Signed and Sealed this

Nineteenth Day of August, 2008

JON W. DUDAS
*Director of the United States Patent and Trademark Office*